United States Patent
Demokritou et al.

(10) Patent No.: US 11,554,190 B2
(45) Date of Patent: Jan. 17, 2023

(54) NANOCARRIERS FOR THE DELIVERY OF ACTIVE INGREDIENTS

(71) Applicant: President and Fellows of Harvard College, Cambridge, MA (US)

(72) Inventors: Philip Demokritou, Brookline, MA (US); Nachiket Dattatray Vaze, Jamaica Plain, MA (US); Georgios Pyrgiotakis, Cranford, NJ (US); Mary Eleftheriadou, Nicosia (CY)

(73) Assignee: President and Fellows of Harvard College, Cambridge, MA (US)

( * ) Notice: Subject to any disclaimer, the term of this patent is extended or adjusted under 35 U.S.C. 154(b) by 284 days.

(21) Appl. No.: 16/640,040

(22) PCT Filed: Aug. 17, 2018

(86) PCT No.: PCT/US2018/046954
§ 371 (c)(1),
(2) Date: Feb. 18, 2020

(87) PCT Pub. No.: WO2019/036654
PCT Pub. Date: Feb. 21, 2019

(65) Prior Publication Data
US 2020/0222566 A1     Jul. 16, 2020

Related U.S. Application Data

(60) Provisional application No. 62/547,512, filed on Aug. 18, 2017.

(51) Int. Cl.
*A61L 2/00* (2006.01)
*B01J 19/08* (2006.01)
(Continued)

(52) U.S. Cl.
CPC ............. *A61L 2/186* (2013.01); *A23L 3/3409* (2013.01); *A23L 3/358* (2013.01); *A61L 2/0088* (2013.01);
(Continued)

(58) Field of Classification Search
CPC ................ A61L 2/00; A61L 2/14; A61L 2/16
(Continued)

(56) References Cited

U.S. PATENT DOCUMENTS

2013/0072563 A1    3/2013  Ho
2014/0325711 A1   10/2014  Schnorr et al.

FOREIGN PATENT DOCUMENTS

WO    WO 2016/044443 A1 *  3/2016  ............... C12Q 1/02
WO    WO-2016044443 A1     3/2016
WO    WO-2019036654 A1     2/2019

OTHER PUBLICATIONS

"European Application Serial No. 18845940.8, Extended European Search Report dated May 11, 2021", 14 pgs.
(Continued)

*Primary Examiner* — Monzer R Chorbaji
(74) *Attorney, Agent, or Firm* — Schwegman Lundberg & Woessner, P.A.

(57) ABSTRACT

Various embodiments of the present invention relate to, among other things, a nano carrier platform for generating enhanced engineered water nanostructures (iEWNS) encapsulating and delivering reactive oxygen species (ROS) and, in some instances, other active ingredients, methods for inactivating at least one of viruses, bacteria, bacterial spores, and fungi on a substrate by applying iEWNS to the substrate.

20 Claims, 17 Drawing Sheets

(51) Int. Cl.
    *A61L 2/18*     (2006.01)
    *A23L 3/3409*     (2006.01)
    *A23L 3/358*     (2006.01)
    *A61L 2/20*     (2006.01)
    *B82Y 5/00*     (2011.01)
    *B82Y 30/00*     (2011.01)

(52) U.S. Cl.
    CPC ............... *A61L 2/208* (2013.01); *B82Y 5/00* (2013.01); *B82Y 30/00* (2013.01)

(58) Field of Classification Search
    USPC ...................................... 422/28, 186, 186.04
    See application file for complete search history.

(56) References Cited

OTHER PUBLICATIONS

"European Application Serial No. 18845940.8, Response to Communcation pursuant to Rules 161 (2) and 162 EPC filed Nov. 2, 2020", 12 pgs.

"International Application Serial No. PCT/US2018/046954, International Preliminary Report on Patentability dated Feb. 27, 2020", 9 pgs.

Pyrgiotakis, Georgios, et al., "Inactivation of Foodborne Microorganisms Using Engineered Water Nanostructures (EWNS)", Environmental Science & Technology, 49(6), (Mar. 17, 2015), 3737-3745.

Pyrgiotakis, Georgios, et al., "Mycobacteria inactivation using Engineered Water Nanostructures (EWNS)", Nanomedicine: Nanotechnology, Biology, and Medicine, 10(6), (Aug. 1, 2014), 1175-1183.

Vaze, Nachiket, et al., "An integrated electrolysis—electrospray—ionization antimicrobial platform using Engineered Water Nanostructures (EWNS) for food safety applications", Food Control, vol. 85, (2018), 151-160.

"International Application Serial No. PCT/US2018/046954, International Search Report dated Jan. 11, 2019", 5 pgs.

"International Application Serial No. PCT/US2018/046954, Invitation to Pay Add'l Fees and Partial Search Report dated Oct. 24, 2018", 3 pgs.

"International Application Serial No. PCT/US2018/046954, Written Opinion dated Jan. 11, 2019", 7 pgs.

Eswaranandam, et al., "Antimicrobial Activity of Citric, Lactic, Malic, or Tartaric Acids and Nisin-incorporated Soy Protein Film Against Listeria monocytogenes", *Escherichia coli*O157:H7, and *Salmonella gaminara*. Journal of Food Science vol. 69, No. 3. (Apr. 2004). FMS79-FMS84.

Pyrgiotakis, et al., "Optimization of a nanotechnology based antimicrobial platform for food safety applications using Engineered Water Nanostructures (EWNS)", Scientific Reports, vol. 6, (2016).

Rudrappa, et al., "Causes and consequences of plant-associated biofiims", FEMS Microbiology Ecology vol. 64, No. 2, (May 2008), 153-166.

"European Application Serial No. 18845940.8, Response filed Dec. 6, 2021 to Extended European Search Report dated May 11, 2021", 15 pgs.

\* cited by examiner

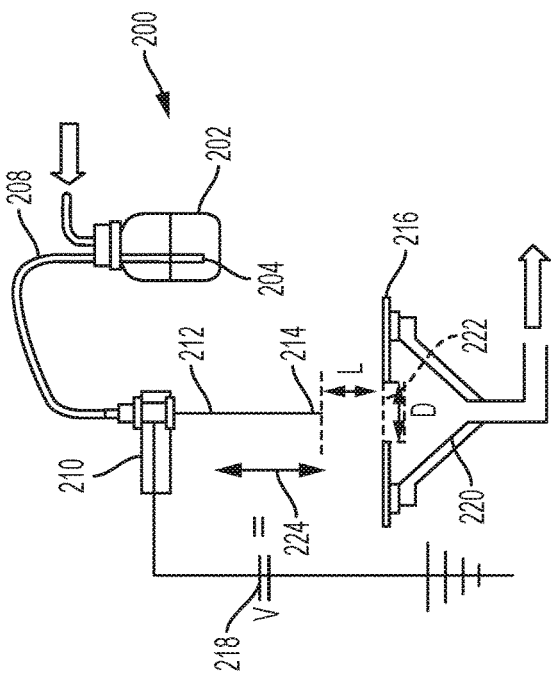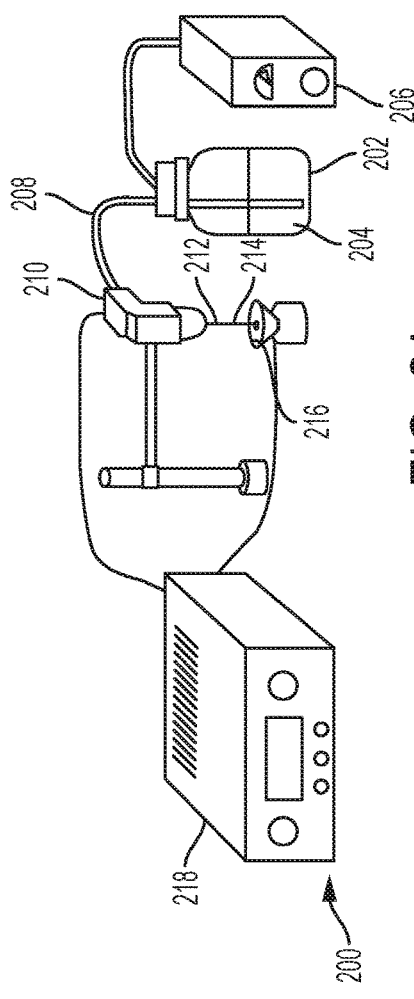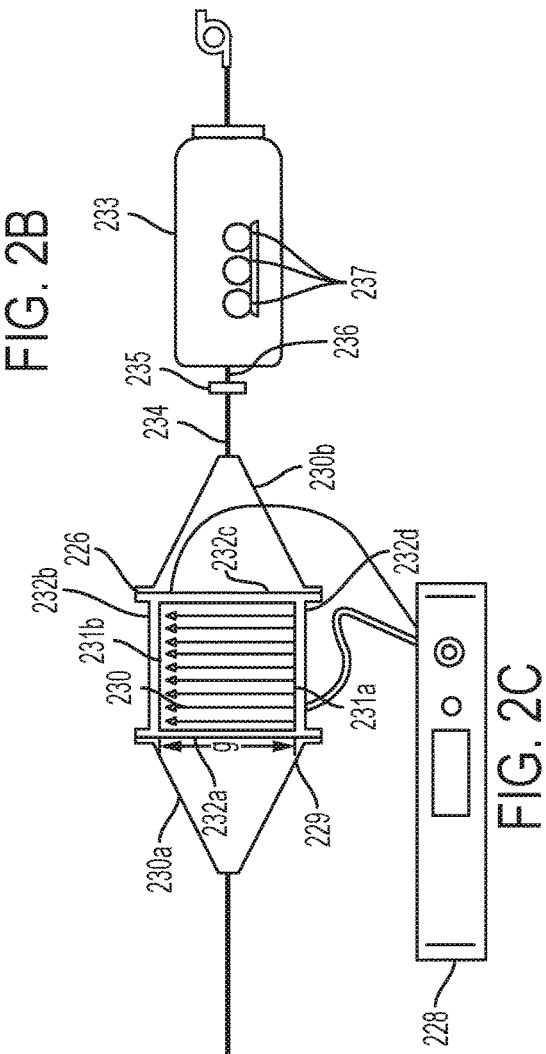
FIG. 2A
FIG. 2B
FIG. 2C

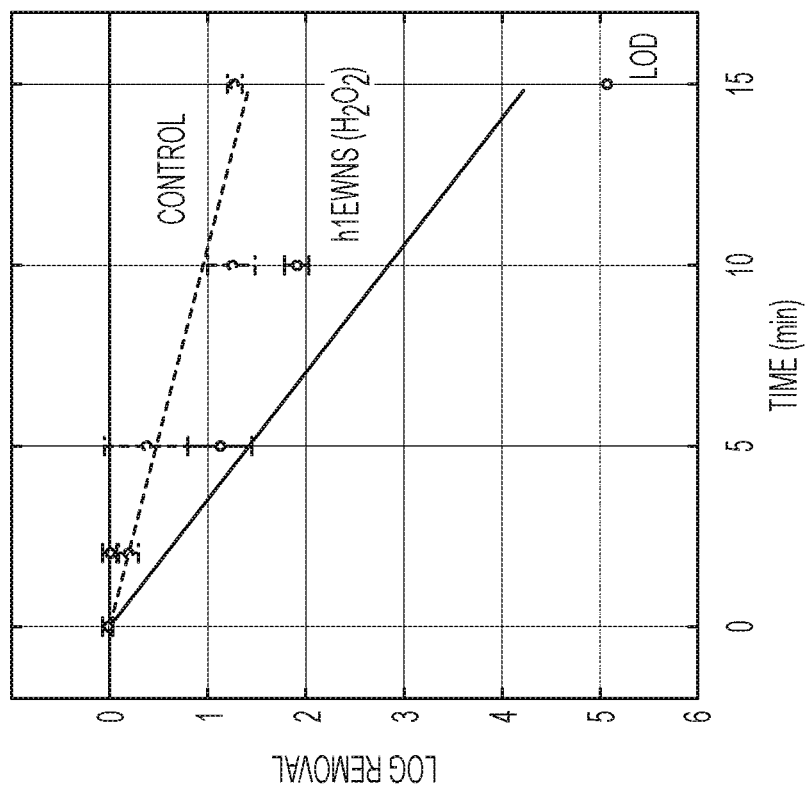
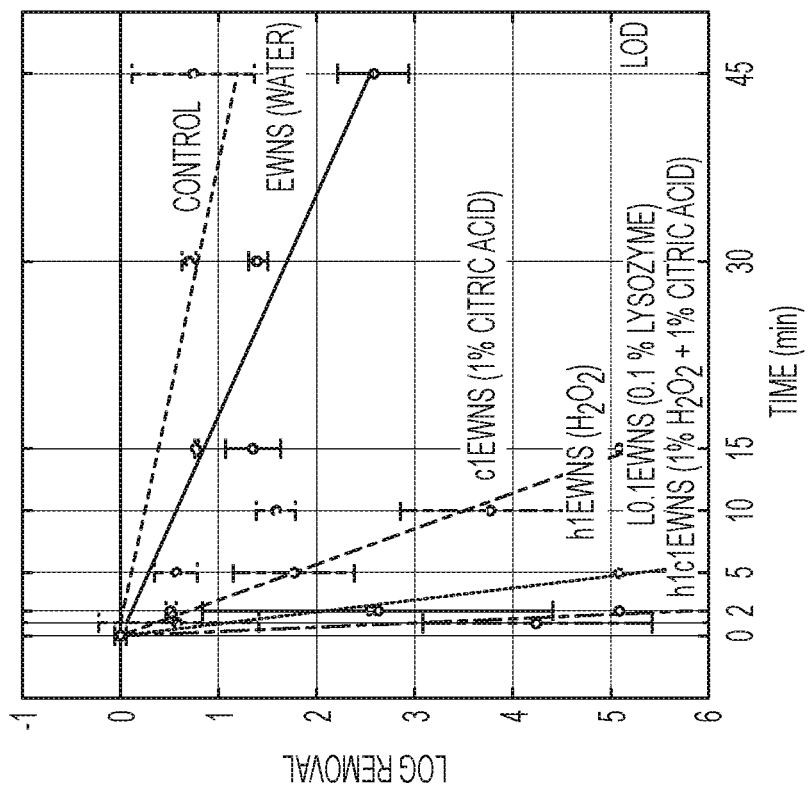
FIG. 9A
FIG. 9B

FIG. 10 ated as WO2019/036654 on Feb. 21, 2019, which claims the benefit of U.S. Appl. Ser. No. 62/547,512, filed Aug. 18, 2017, the entireties of both of which are incorporated by reference as if set forth herein.

NANOCARRIERS FOR THE DELIVERY OF ACTIVE INGREDIENTS

CROSS-REFERENCE TO RELATED APPLICATIONS

This application is a U.S. National Stage Filing under 35 U.S.C. § 371 from International Application No. PCT/US2018/046954, filed on Aug. 17, 2018, and published as WO2019/036654 on Feb. 21, 2019, which claims the benefit of U.S. Appl. Ser. No. 62/547,512, filed Aug. 18, 2017, the entireties of both of which are incorporated by reference as if set forth herein.

BACKGROUND OF THE INVENTION

Infectious disease transmission is one of the biggest challenges to public health globally. Microorganisms are responsible for a large number of food related outbreaks. From 2004-2012, the United States saw 377 major food related outbreaks, with Noroviruses, *Salmonella* and *E. coli* being the biggest culprits. By a 2014 USDA estimation, foodborne illnesses cost the economy $15.6 billion annually. Each year, more than 8.9 million Americans fall ill as a result of the presence of 15 major pathogens found in food. Furthermore, microorganisms have also become a major hurdle in the medical field causing health acquired infections, a major problem in healthcare systems, worldwide. Microorganisms are constantly adapting to current antimicrobial technologies and antibiotics, leading to ineffectiveness of treatment and persistence of infection. These infections potentially cause severe morbidity and even mortality.

Currently, there are various antimicrobial strategies being employed in the field. These include chemicals such as Chlorine-elemental, hypochlorite-chlorine dioxide and acid washes, hydrogen peroxide in liquid or vapor form, as well as UV radiation based technologies. Chemicals such as Chlorine leave behind chemical residues, are not effective with a heavy organic load and are not approved for organic products due to restrictions imposed by regulations for organic produce. Ultraviolet radiation cannot be used for the treatment of sensitive material such as skin, since it causes damage to the DNA. Recently, nanotechnology based approaches, which utilize nanoparticles such as silver and photocatalytic $TiO_2$, have emerged. However, these nanoparticle based approaches have limitations, related to delivery of nano-aerosols or chemical residues, subsequent ingestion, and unintended toxicity. These drawbacks underscore the importance of developing technologies that are cost-effective, easy to produce, and in some instances, chemical free. Especially for food applications, there is a need to produce a "green" technology that is attractive in terms of energy consumption; waste minimization; leaves little to no residue; and has little or no unintended toxicity.

BRIEF DESCRIPTION OF THE FIGURES

The drawings illustrate generally, by way of example, but not by way of limitation, various embodiments discussed in the present document.

FIGS. 2A-2B are schematic of a potential system 200 for generating EWNS and, optionally, applying EWNS to a target, in an example embodiment for pathogen inactivation.

FIG. 2C is a schematic showing the ability of the EWNS to be generated at one location and "transported" to another location for delivery.

FIGS. 7A-7B denote the change in the Firmness and Internal pH after treatment with EWNS. FIGS. 7C-7D denote the change in Firmness and Color after treatment with hEWNS (in this case, h1EWNS, produced with 1% $H_2O_2$). The results were measured using visual analysis of the redness of tomatoes (color) and through penetrometer output post-puncture (firmness). The internal pH was measured by testing the juice of the tomatoes with a pH measuring strip. The results indicate that there is no significant difference in the color or firmness after hEWNS treatment.

FIGS. 9A-9D are plots of log reductions/removal as a function of time. The summary of the surface inactivation produced by various iEWNS: (A) inactivation of *E. coli* produced by various iEWNS; inactivation produced by h1EWNS against (B) *L. innocua;* (C) *A. baumannii* and (D) Influenza H1N1/PR/8. The initial inoculum was $10^6$ cfu, expect for the case of Influenza (105 IU). (n=3).

FIG. 10 is a bar graph showing rates of inactivation produced by iEWNS in *E. coli* (red columns) and the dose required for producing 3 log reduction (99.9% removal) in *E. coli* (blue columns).

DESCRIPTION

Figure 1A:
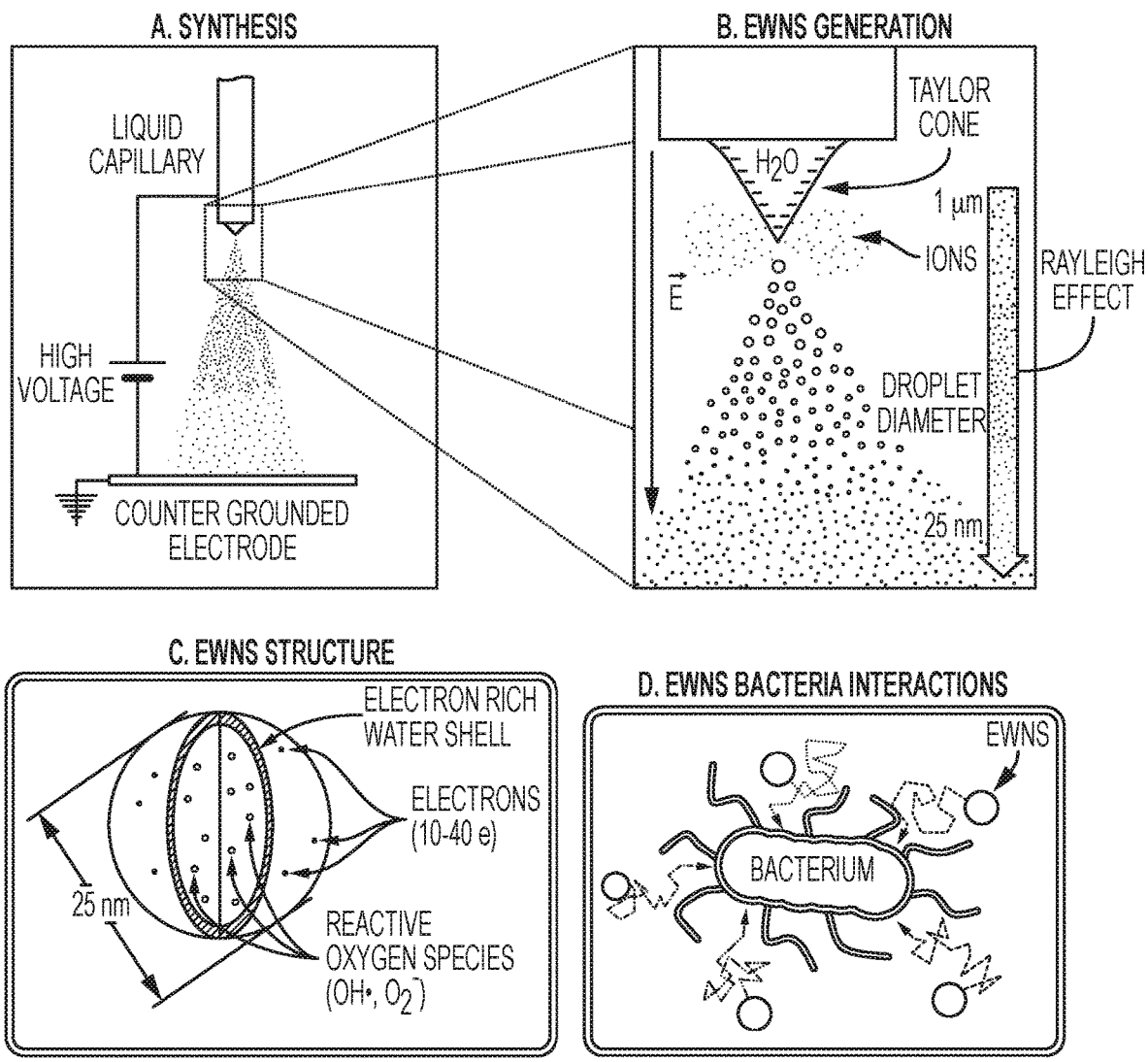
FIG. 1A is a schematic of a system for the synthesis of the basic EWNS of the various embodiments and their interactions with pathogens, in this case, bacteria. This system has been described in PCT Appl. No. WO 2016/044443, which is incorporated by reference as if fully set forth herein.
Figure 1B:
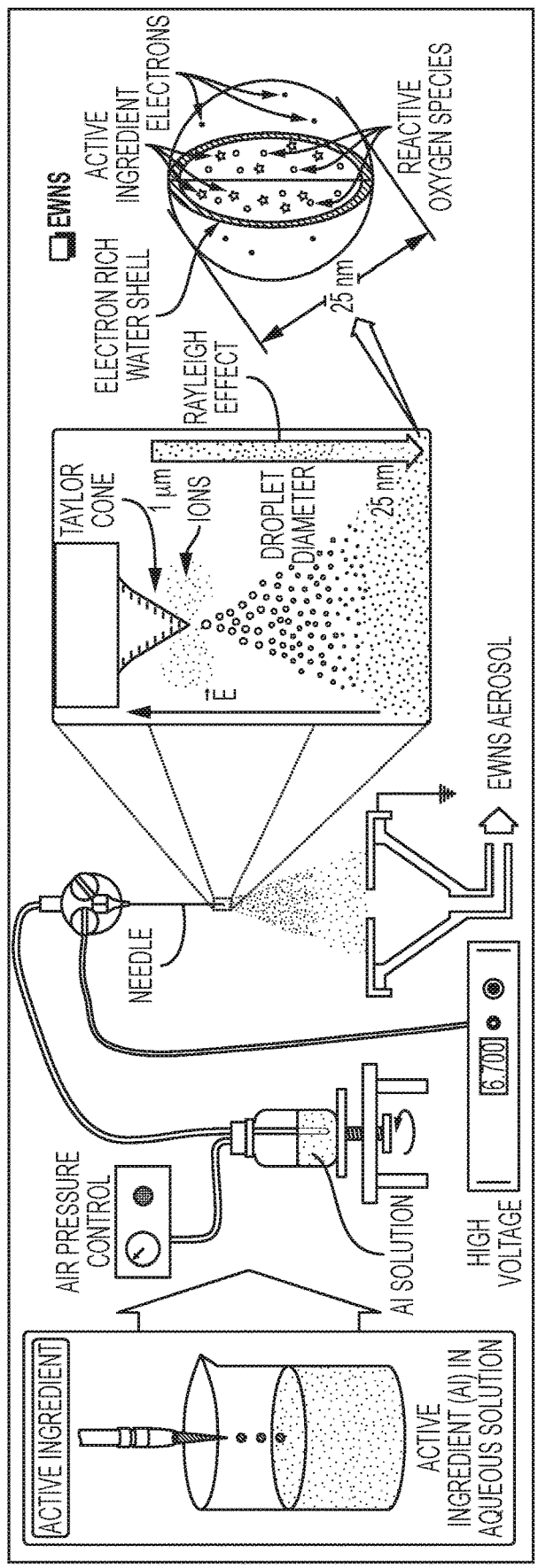
FIG. 1B is a schematic of the of the "nano-carrier" platform described herein, indicating the synthesis of iEWNS which contain the encapsulated Active Ingredient (AI), as well as the Reactive Oxygen Species generated from the aqueous phase. (The "i" in front of EWNS depicts the encapsulation of "i" (AI). For example, hEWNS depicts encapsulation of $H_2O_2$ in the EWNS)

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The various embodiments of the present invention provide, among other things approaches for significantly reducing the microbial load on various substrates, including the surface of foodstuffs (e.g., fresh produce, including raw or minimally processed fruit or vegetables); skin (e.g., on healthy skin or wounded skin containing chronic ulcers, skin diseases, skin burns, and the like to, among other things, facilitate or accelerate the wound healing process); interior surfaces (e.g., home or business surfaces, including countertops); and air (e.g., air handling systems, such as air conditioning systems). The various embodiments of the present invention achieve these goals by using engineered water nanostructures (EWNS) as nanocarriers to deliver active ingredients to a surface/substrate, thereby reducing the microbial load on such surfaces/substrates.

Other embodiments provide approaches for significantly reducing the formation of biofilms produced by bacteria and/or significantly reducing the strength of the biofilms produced by bacteria by treating a bacteria-infected area (e.g., on wounded skin) with the EWNS described herein. In such approaches, at least the film formation can be reduced by at least 50%, at least 60%, at least 70%, at least 80%, at least 90% or at least 99% or higher; or from about 50% to about 100%, about 60% to about 90%, about 70% to about 99% or about 80% to about 95%.

It should be understood that, although the various embodiments of the present invention provide, among other things, "chemical-free" approaches for significantly reducing the microbial load on the substrates described herein, the methods described herein can also be used in conjunction with soap and water, as well as other chemical-based anti-infective methods, including topical antiseptics and systemic antibiotics.

Briefly, EWNS are generated, in some embodiments, by electrospraying water from the tip of an electrode. A high negative voltage (e.g., −5 to −10 kV) is then applied between the two electrodes placed, e.g., about 4 mm apart. The strong electric field between the two electrodes causes negative charges to accumulate on the surface of the condensed water that is held on the electrode by surface tension. As a result, highly charged water droplets form and continue to break into smaller particles. At optimum conditions of water flow and electric field, EWNS can reach nanoscale size objects and possess unique physico-chemical and morphological properties. Concurrently with the generation of water droplets, the electric field conditions can be manipulated so that water molecules are split and electrons removed, resulting in a high number of reactive oxygen species (ROS) (ionization process). EWNS are highly mobile due to their nanoscale size and remain suspended in the air for hours (extended lifetime) due to their increased surface charge which reduces evaporation. The concurrently generated, ROS are encapsulated in the EWNS. EWNS generated in this fashion are highly charged and carry an average of 10 to over 80 electron charges per nanostructure. In addition, the EWNS are loaded with at least three ROS species, namely, hydroxide radicals (OH.), superoxide ($O_2^-$), and hydrogen peroxide ($H_2O_2$). As used herein, the term "reactive oxygen species" and "ROS" generally refers to any reactive oxygen species that can be generated in water droplets using the EWNS generating methods described herein. ROS therefore include, but are not limited to, hydroxide radicals (OH.), superoxide ($O_2^-$), and hydrogen peroxide ($H_2O_2$).

ROS such as hydroxide radicals and superoxide are known for their ability to inactivate bacteria on surfaces, as occurs in $TiO_2$ photocatalysis. Electrospray properties, namely, electric field and water flow rate, can be optimized to result in EWNS that are polydisperse in size and exhibit a log normal distribution (e.g., with a mean 25 nm, a mode of 23 nm, and a standard deviation of 9 nm). Without wishing to be bound by any particular theory, it is believed that the polydispersity is due to the variation of the surface charge, the randomness of the Rayleigh effect, and the inevitable evaporation over time. In addition, EWNS generated in this fashion are stable in size with very minimal evaporation under ambient conditions (e.g., 25° C. and 1 atm). An active ingredient 'I' in aqueous suspension is taken through the EWNS synthesis platform described herein and as a result such AI is encapsulated in the EWNS forming the iEWNS which contain in addition to the ROS the encapsulated AI. This nano carrier approach encapsulates AI and turns them in a nanoscale aerosol (iEWNS) with unique physico-chemical and antimicrobial properties as a result of the synergistic effects of both the AI and the ROS from aqueous phase. The electric charge of the generated iEWNS can be used to target the delivery to a surface of interest (e.g., fresh produce, wound, etc.) using an electric field.

Some embodiments are directed to a method for inactivating at least one of viruses (e.g., influenza H1N1/PR/8 virus), bacteria, bacterial spores, and fungi (e.g., yeasts and molds) on a substrate comprising: encapsulating reactive oxygen species (ROS), produced using electrolysis of water, into engineered water nanostructures (rEWNS) having a surface charge and using the surface charge to target the delivery to the substrate to inactivate the at least one of viruses, bacteria, bacterial spores, and fungi. In this method, the AI to be encapsulated is ROS pre-generated through the electrolysis of de-ionized water and additional amounts of ROS are generated from the aqueous phase of the suspension. It should be noted that the "r" in "rEWNS" refers to the ROS produced using electrolysis of de-ionized water and that are encapsulated in the EWNS.

Electrolysis of deionized water can be used to generate the ROS in solution. It is worth noting that similar approaches have been used in the form of electrolyzed water to treat in a wet manner fresh produce such as lettuce, bell peppers and cucumber. Huang Y -R, et al., *Food Control* 19: 329-345 (2008), which is incorporated by reference as if fully set forth herein. However, such approaches involve the addition of salts (e.g., NaCl) and acids (e.g., acetic acid) to the water that leave behind a range of chemical residues that are not compatible with organic produce. Furthermore, the electrolyzed water approach is a "wet" method, and the fresh produce is either dipped in, or rinsed with electrolyzed water. Such wet methods can damage sensitive produce, such as berries, that cannot tolerate wet disinfection treatment, affecting sensory characteristics, leaving chemical residues and demanding large volumes of electrolyzed water, which increases the energy requirements.

ROS can be produced using any known method for the electrolysis of water, including electrolysis of water; exposure of water to infrared or UV light (Gudkov et. al., Biophysics, 2012, Vol. 57, No. 1, pp. 1-8); and via the use of Xanthine Oxidase that produce ROS in biological media. In some examples, water (e.g., deionized water) is electrolyzed using a two-electrode assembly. The electrodes can be powered by a high-voltage DC power supply (e.g., at 600 V DC). Suitable current is drawn through the water (e.g., current ranging from about 0.2 A to about 1.7 A). Such current will introduce chemical alteration in the water structure and create ROS. The chemical composition and ROS content of the electrolyzed water and the resulting rEWNS can be parametrically investigated with Electron Paramagnetic Resonance (EPR) and Trolox Equivalent Antioxidant Capacity (TEAC) methods, as a function of the applied voltage and electrolysis time. The electrospray and ionization that takes place during the rEWNS synthesis will further increase the ROS content and other properties of rEWNS and therefore, increase their potency.

Other embodiments are directed to a method for inactivating at least one of viruses, bacteria, bacterial spores, and fungi on a substrate comprising: applying enhanced engineered water nanostructures (iEWNS) for a targeted and precise delivery to the substrate to inactivate at least one of viruses, bacteria, bacterial spores, and fungi; the iEWNS comprising (i) reactive oxygen species (ROS), (ii) at least one active ingredient in addition to the ROS, and (iii) a surface charge. The notation "iEWNS" refers to EWNS that have been enhanced with at least one active ingredient in addition to the ROS. The "i" in the "iEWNS" is shorthand for the at least one active ingredient encapsulated in addition to the ROS generated from aqueous phase of suspension. Accordingly, if the at least one active ingredient is $H_2O_2$, the iEWNS is referred to as "hEWNS" herein. If, on the other hand, the at least one active ingredient is citric acid, the iEWNS is referred to as cEWNS herein. If, on the other hand, the at least one active ingredient is ROS produced using electrolysis of water, the EWNS is referred to as rEWNS herein. But it should be clear that the term EWNS, without an "r" or an "x" generally refers to rEWNS and iEWNS. Finally, when the iEWNS nomenclature includes a number, the number refers to the concentration, in terms of weight per unit volume, of the at least one active ingredient in a composition used to generate the iEWNS. Thus, for example, "h1EWNS" refers to hydrogen peroxide ($H_2O_2$) encapsulated in EWNS, where the hydrogen peroxide composition used to generate the h1EWNS is a 1% w/v hydrogen peroxide composition.

As used herein, the term "bacteria" generally refers to gram-positive and gram-negative bacteria. Gram-positive bacteria include, but are not limited to, mycobacteria. Mycobacteria, in turn, include, but are not limited to, *M. africanum, M. avium, M. bovis, M. chelonei, M. farcinogenes, M. flavum, M. fortuitum, M. haemophilum, M. intracellulare, M. kansasii, M. leprae, M. lepraemurium, M. marinum, M. microti, M. parafortuitum, M. paratuberculosis, M. phlei, M. scrofulaceum, M. senegalense, M. simiae, M. smegmatis, M. thermoresistibile, M. tuberculosis, M. ulcerans,* and *M. xenopi*. Other gram-positive bacteria include, but are not limited to, gram-positive cocci including *Staphylococcus aureus,* methicillin-resistant *Staphylococcus aureus* (MRSA), Group A *Streptococci,* Group B *Streptococci,* Group C *Streptococci,* Group G *Streptococci,* and vancomycin resistant Enterococci (VRE). Other gram-positive bacteria include *Listeria* spp. (e.g., *Listeria monocytogenes, Listeria innocua*), *Clostridium* spp. (e.g., *Clostridium perfringens* and *Clostridium botulinum*), and *Bacillus cereus*.

Gram-negative bacteria include, but are not limited to, *Pseudomonas aeruginosa, Pseudomonas* spp., *Serratia marcescens, E. coli, Salmonella* spp., *Campylobacter jejuni, Shigella,* and *Vibrio* spp.

In some embodiments, the bacteria are at least one of *Escherichia coli, Listeria innocua, Listeria* spp. *Salmonella enterica, Salmonella* spp., *Mycobacterium parafortuitum, Saccharomyces cerevisiae, Pseudomonas aeruginosa, Pseudomonas* spp., *Serratia marcescens, Staphylococcus aureus,* methicillin-resistant *Staphylococcus aureus* (MRSA), *Staphylococcus epidermitis,* methicillin-resistant *Staphylococcus epidermidis* (MRSE), *Propionibacterium acnes,* Group A *Streptococci,* Group B, *Streptococci,* Group C *Streptococci,* Group G *Streptococci,* vancomycin resistant Enterococci (VRE), and *Acinetobacter baumannii*.

Viruses include, but are not limited to, norovirus, influenza virus, bacteriophages, and a hepatitis virus (e.g., hepatitis A virus).

As used herein, the term "yeasts" generally refers to organisms such as *S. cerevisiae* and the like from the fungi family.

As used herein, the term "active ingredient" encompasses, but is not limited to, an antimicrobial active ingredient. Examples of antimicrobial active ingredients include, but are not limited to, hydrogen peroxide in addition to any hydrogen peroxide that is generated when the EWNS are generated, one or more inorganic antimicrobials (e.g. nanoparticles such as silver and photocatalytic $TiO_2$), one or more organic acids and salts thereof (e.g., lactic acid, acetic acid, citric acid, sodium lactate, potassium lactate, buffered sodium citrate, and acidified sodium chlorite), one or more chemical antimicrobials (e.g., trisodium phosphate, chlorine dioxide, peracetic acid, and sodium nitrite), one or more ovo antimicrobials (e.g., lysozyme), one or more lacto antimicrobials (e.g., lactoferrin), one or more bacto antimicrobials (e.g., nisin, pediocin, sakacin, reuterin, lacticin, macedocin and colicin), and one or more phyto antimicrobials, inorganic colloids, emulsions or combinations thereof. For example, contemplated herein are combinations of two or more of the aforementioned active ingredients, such as a combination of hydrogen peroxide and citric acid.

Phyto antimicrobials include, but are not limited to, compounds found in spices including allspice, bay leaves, capsicums, cinnamon, cloves, cumin, garlic, lemon grass, onion, oregano, rosemary, tarragon, and thyme; compounds found in essential oils, including eugenol, carvacrol, thymol, and vanillin; tannins and polyphenolic compounds such as catechin, catechin gallate, caffeine, chlorogenic acid, epicatchin, epicatechin gallate, epigallocatechin gallate, gallic acid, gallocatechin, theaflavin theobromine, and theophylline; prune extracts; and hop acids, including hops beta acids such as lupulone, colupulone, and adlupulone.

The term "substrate" as used herein encompasses any surface, such as cloth (e.g., in clothes); medical products (e.g., gauze and tape); medical instruments; medical devices; the surface of a wound; a skin surface (e.g., unwounded skin or tissue); and surfaces of foodstuffs (e.g., fruit, vegetables, and meats), surfaces employed during the processing of foods. But the term "substrate" also encompasses gaseous substrates, including air.

As used herein, the term "wounds" or "wound" generally refers to wounds resulting from trauma, a surgical procedure, an infectious disease or an underlying condition. The term "wounds" or "wound" encompasses open wounds as well as closed wounds, such as sutured or stapled wounds. Examples of open wounds include punctures, abrasions, cuts, lacerations, and burns. The term "wounds" or "wound" also encompasses chronic wounds, such as pressure ulcers, diabetic ulcers, arterial ulcers, venous ulcers or combination of all the above.

As used herein, the term "in a wound" refers to inside a wound, in the periphery of a wound or near a wound.

The methods of the various embodiments of the present invention are also generally directed to a method for inactivating at least one of at least one of viruses, bacteria, bacterial spores, and fungi on a subject's unwounded tissue before the unwounded tissue is wounded by, e.g., surgery. The various methods of the present invention, therefore, provide methods for disinfection of tissue (e.g., skin) in general and, in particular, for disinfection of tissue prior to or during surgery.

Various other embodiments are directed to inactivating at least one of viruses, bacteria, bacterial spores, and fungi on produce. And the method can be employed at any point in the production of the produce; that is, from "field to fork."

As used herein, the term "produce" includes, but is not limited to, fruit and vegetables including: avocado and pome fruits such as apples and pears; nectarines and peaches; vegetables from the Solcanaceae family, for example, potatoes, peppers, eggplants and tomatoes; vegetables from the Alliaceae family, such as onions; vegetables from the Brassiaceae family also referred to as the Cruciferae family, for example cabbage; vegetables from the Cucurbitaceae family, for example, cucumbers; vegetables from the Apiaceae family also referred to as the Umbelliferae family, for example celery; the Compositae family, also referred to as the Asteraceae family, for example, lettuce; and edible fungi of the Ascomycetes/Basidiomycetes classes.

Even though the methods of method for inactivating at least one of viruses, bacteria, bacterial spores, and fungi described herein can be applied to produce, they can also be applied to inactivating at least one of viruses, bacteria, bacterial spores, and fungi on other food including, but not limited to, meat (e.g., beef, chicken, and pork) and other foodstuffs at any point in their production; that is, from "farm to fork."

As used herein, the term "subject" generally refers to a human, non-human primate, rat, mouse, cow, horse, pig, sheep, goat, dog, cat, etc. In some embodiments, the subject is preferably a human subject.

In some embodiments, the EWNS are applied to a substrate at a concentration of about 5,000 to about 500,000 EWNS per mL of air surrounding or around the substrate. In some embodiments, the EWNS are applied to a substrate at a concentration of about 5,000 to about 100,000 EWNS per mL, about 5,000 to about 10,000; about 5,000 to about 50,000; about 10,000 to about 50,000; about 25,000 to about 100,000; or about 5,000 to about 25,000 EWNS per mL; about 100,000 to about 500,000; about 500,000 to about 1,000,000 EWNS per mL; about 17,000 to about 24,000 EWNS per mL; or about 42,000 to about 60,000 EWNS per mL (e.g., EWNS per mL of air surrounding or around the substrate, as described herein).

In some embodiments, the total ROS concentration in rEWNS is from about 20 µM to about 50 µM after sampling of the rEWNS particles by bubbling the particles through a solution of Trolox placed inside a glass impinger for about 5 minutes to about 15 minutes, at the rate of 0.5 Liters per minute airflow and analyzing thus trapped particles with Trolox Quinone method. In other embodiments, enhanced EWNS (iEWNS) deliver a total dose of the at least one active ingredient to the substrate of from about 1 pg to about 1 µg (e.g., about 100 pg to about 100 ng; about 500 pg to about 500 ng; or about 500 ng to about 1 µg) in about one hour or less (e.g., in about 45 minutes or less; in about 30 minutes or less; in about 10 minutes or less; or in 1 minute or less).

In some embodiments, when the EWNS are applied to a substrate (e.g., at the aforementioned concentration(s)), the application results in a reduction of the number of colony forming units (cfu) on the substrate by ≤about 1 to about 5 $\log_{10}$ compared to control (e.g., a reduction in the number of cfu on the substrate of about 1 $\log_{10}$ to about 5 $\log_{10}$; about 1 $\log_{10}$ to about 5 $\log_{10}$; 2 $\log_{10}$ to about 5 $\log_{10}$; about 1 $\log_{10}$ to about 1.5 $\log_{10}$; about 1.5 $\log_{10}$ to about 3 $\log_{10}$; about 2 $\log_{10}$ to about 3 $\log_{10}$; about 1 $\log_{10}$ to about 2.5 $\log_{10}$; or about 1 $\log_{10}$ to about 2 $\log_{10}$, compared to control).

In some embodiments, when the EWNS are applied to a substrate (e.g., at the aforementioned concentration(s)), the application results in a reduction of the number of cfu on the substrate at a rate of from about 0.05 $\log_{10}$/min to about 1.01 $\log_{10}$/min, compared to control (e.g., a reduction of the number of cfu on the substrate at a rate of from about 0.05 $\log_{10}$/min to about 0.5 $\log_{10}$/min; 0.05 $\log_{10}$/min to about 0.1 $\log_{10}$/min; about 0.1 $\log_{10}$/min to about 0.5 $\log_{10}$/min; about 0.1 $\log_{10}$/min to about 0.3 $\log_{10}$/min; or about 0.5 $\log_{10}$/min to about 1 $\log_{10}$/min, compared to control).

In some embodiments, when the EWNS are applied to a substrate (e.g., at the aforementioned concentration(s)), the application results in a reduction in the number of cfu on the substrate that is at least twice the reduction observed for EWNS that are not rEWNS or iEWNS after a 45 minute treatment of the substrate. In other embodiments, when hEWNS are applied to a substrate (e.g., at the aforementioned concentration(s)), the application results in a reduction in the number of cfu on the substrate at least 5 $\log_{10}$ cfu after a 5 minute treatment of the substrate.

The EWNS of the various embodiments of the present invention can be applied to a substrate for any suitable time period over which a suitable $\log_{10}$ reduction in the number of cfu is observed. Examples of suitable time periods over which a suitable $\log_{10}$ reduction in the number of cfu is observed include about 30 seconds to about 5 hours; about 1 minute to about 180 minutes; about one minute to about 20 minutes; about 10 minutes to about 180 minutes (3 hours); about 1 hour to about 5 hours; about 30 seconds to 5 minutes; about 1 hour to about 3 hours; or about 30 minutes to 1 hour.

In some embodiments, the electric charge of the EWNS of the various embodiments of the present invention is from about 10 to about 40 e−; about 10 to about 25 e−; about 20 to about 40 e−; or about 10 to about 30 e−.

The EWNS of the various embodiments of the present invention can be applied to a substrate (e.g., skin, a wound, produce or meat) using any suitable means including, but not limited to electrostatic precipitation or diffusion, or a combination of both, using any suitable method, including the methods described herein.

Other method of the various embodiments of the present invention are directed to inactivating at least one of viruses, bacteria, bacterial spores, and fungi on any surface that cannot otherwise be disinfected using conventional methods (e.g., chlorine; chlorine dioxide; peracetic acid; hydrogen peroxide; quaternary ammonium compounds for wash water; ozone; and irradiation) because such conventional treatment could cause damage to the surface. Such surfaces include any surfaces on or around works of art, archaeological artifacts, museum artifacts, and the like.

The EWNS of the various embodiments of the present invention can be generated by any suitable method known in the art and using any suitable electro spray device known in the art, including the methods and devices described herein. One method and device known in the art for the generation of EWNS are described in U.S. Pat. No. 7,473,298, which is incorporated by reference as if fully set forth herein.

FIGS. 2A-2B depict aspects of a system 200 for generating EWNS and, optionally, applying EWNS to a target, in an example embodiment.

FIG. 2A depicts the system 200 generally. A fluid source 202 is configured to contain fluid 204, such as electrolyzed water or water comprising one or more active ingredients, as disclosed herein. A source of pressure 206 is configured to place the fluid 204 in the fluid source 202 under pressure, forcing the fluid 204 up a tube 208 to a fluid emitter 210.

The fluid emitter 210 includes a conduit 212 fluidly coupled to the fluid source 202. In various examples, the conduit 212 is a capillary, needle, or other elongate tube that includes a lumen through which fluid 204 from the fluid source 202 may pass. In various examples, the conduit 212 is a metallic capillary or metallic needle or is made of any of a variety of electrically conductive substances. The conduit 212 includes an aperture 214 through which the fluid 204 exits the conduit 212.

The conduit 212 is positioned with respect and in relation to an electrode 216. In FIG. 2B, the conduit 212 is shown to be at a 0 degree angle with regard to vertical axis 224 and at a 90 degree angle with regard to the electrode 216. But the conduit 212 can be positioned at any suitable angle in relation to vertical axis 224 (e.g., ±45 degrees). Fluid 204 that exits the conduit 212 via the aperture 214 comes into proximity of the electrode 216. A variable voltage source 218 is coupled between the conduit 212 and the electrode 216 to induce an electric potential between the conduit 212 and the electrode 216. Fluid 204 that passes through the conduit 212 and in proximity of (including potentially in contact with) the electrode 216 is energized and changes state to EWNS, as disclosed herein. The EWNS (e.g., rEWNS and iEWNS) are then collected in a fluid collection member 220.

FIG. 2B is a detailed depiction of aspects of the system 200. As illustrated, the conduit 212 has a first end coupled to the fluid emitter and a second end opening up with the aperture 214 and is positioned above the electrode 216. The aperture 214 is directly above an electrode aperture 222 in the electrode 216 along a vertical axis 224. In the illustrated example, the electrode aperture 222 is circular having a diameter D, though in various examples the electrode aperture 222 may have any of a variety of shapes and sizes as desired. In some instances, the diameter D can be changed to enhance the field strength from about 1% to about 10% as the diameter is changed.

A distance between the aperture 214 and the electrode 216 defines a distance L. The distance L is predetermined and adjustable based on a relative position of the aperture 214 with respect to the electrode 216. In various examples, either or both of the conduit 212 and the electrode 216 are repositionable or adjustable. Thus, the distance L may be adjusted by repositioning one or both of the conduit 212 and the electrode 216.

While the distance L is depicted as being along the vertical axis 224, it is noted and emphasized that the distance L may have a horizontal component, in part or in whole. In various examples, the source of pressure 206 may be such that fluid 204 is expelled from the aperture with sufficient force that the fluid 204 may travel a horizontal distance from the aperture 214 before coming in proximity of the electrode 216, in which case the distance L may include a horizontal component.

The applied voltage V from the voltage source 218 and resultant electric potential between the conduit 212 and the electrode 216, the distance L, the electrode aperture 222 diameter D, and the flow rate of the fluid 204 through the aperture 214 may all be adjustably varied to generate nanoscale size EWNS. Those components may be adjusted to seek, among other things, to impart a relatively high charge and ROS content to the EWNS.

The system 200 generates an electric field between the conduit 212 and the electrode 216. The strength of the electric field is related to the applied voltage V; the distance L; and the overall geometry of the electrode 216 and the electrode aperture 218. In some embodiments, the electric field strength is from about $1 \times 10^5$ V/m to about $6 \times 10^5$ V/m; e.g., from about $1.5 \times 10^5$ V/m to about $5 \times 10^5$ V/m; about $2 \times 10^5$ V/m to about $4.5 \times 10^5$ V/m; or about $2 \times 10^5$ V/m to about $5 \times 10^5$ V/m.

FIG. 2C illustrates a "draw through" Electrostatic Precipitation Exposure System (EPES) 226 which can be used for targeted delivery of EWNS on surfaces. The EPES 226 utilizes the electric charge of the EWNS and with the application of an electric field, it can directly "guide" them to the target surface. Details of the EPES system 226 are discussed in greater detail in G. Pyrgiotakis, et al., *Environ. Sci. Technol.* 49: 3737-3745 (2015), which is incorporated by reference as if fully set forth herein. Briefly, in some examples the EPES 226 consists of a chamber 229 (e.g., PVC chamber), which has tapered ends 230a and 230b and contains two parallel plates 231a and 231b (e.g., stainless steel metal plates such as stainless steel 304, mirror finish) in the center, placed at distance g from one another (e.g., 15.24 cm apart). The plates 231a and 231b are connected to voltage source 228 (Bertran 205B-10R, Spellman, Hauppauge, N.Y.), with the plate 231a connected to positive voltage and the plate 231b connected to ground (e.g., floating ground). In some examples, the outside walls 232a-d of the chamber were coated with a metal foil (e.g., aluminum foil) that was electrically grounded to prevent particle loses. The chamber 227 has, in some examples, a front door (e.g., an airtight front-loading door; not shown) that allows the test surfaces (e.g., produce) to be placed on an elevated surface (e.g., a plastic rack; not shown) that keeps the test surfaces elevated from the plate 231a in order to avoid interference from the high voltage.

The deposition efficiency of the EWNS in the EPES was calculated according to the protocols described in G. Pyrgiotakis, et al., *Environ. Sci. Technol.* 49: 3737-3745 (2015), which is incorporated by reference as if fully set forth herein.

In some examples, a second chamber 233 can be connected in series via conduit 234 to the EPES system 226, utilizing a filter 235 (e.g., a HEPA filter) at the inlet 236 to the second chamber 233 to remove the EWNS. This second chamber 233 can be used as a control chamber for pathogen inactivation experiments and has identical atmosphere (T and RH) as the EPES, but without the EWNS. See FIG. 2C, where, for example, produce 237 is placed.

In some embodiments the deposition/applying efficiency is from about 50% to about 100% (e.g., from about 50% to about 90%; about 80% to about 99%; or about 90% to about 100%) with 3 kV voltage and 0.5 L/min flow rate. In other embodiments the deposition/applying efficiency is from about 50% to about 100% (e.g., from about 50% to about 90%; about 80% to about 99%; or about 90% to about 100%) with 5 kV voltage and 0.5 L/min flow rate. As used herein, the term "deposition/applying efficiency" refers to the percentage of EWNS generated that are deposited/applied to a wound, produce or meat or surface of interest.

Figure 3:
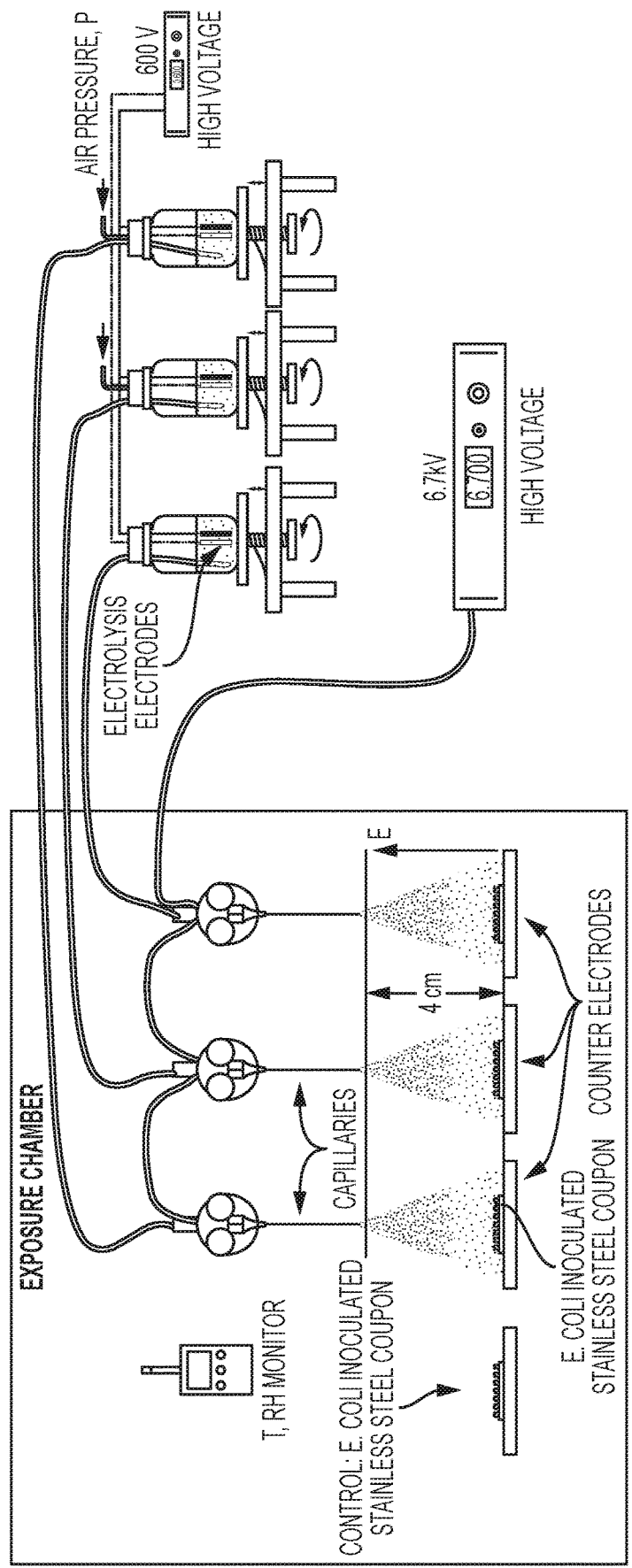
FIG. 3 is a schematic of a multi-capillary system, showing the treatment/exposure methodology for stainless steel coupons inoculated with *E. coli*.

In some examples, the surface of interest (e.g., fruit, wound etc.) can be placed directly under the needle and the same electric field that is used to generate the iEWNS can be used for direct targeted delivery of the iEWNS on the surface of interest as depicted in FIG. 3. The iEWNS particles are generated at the tip of the electrospray capillary (needle). These particles have surface charge that is utilized to direct them towards the grounded electrode. The electric field gradient ('E' in FIG. 3) between the positively charged electrospray needle and the grounded electrode causes the particles to be deposited on the surface in a directed manner. The flow of these particles is vertically downwards onto the SSC kept on the grounded electrode.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about" as used herein can allow for a degree of variability in a value or range, for example, within 10%, within 5%, or within 1% of a stated value or of a stated limit of a range.

The application of hEWNS to substrates such as produce and meat causes no significant deterioration in the sensory quality of the produce or meat. In some instances, the application of hEWNS to substrates such as produce and meat causes about 0% deterioration in the sensory quality of the produce or meat, using methods known in the art for determining the deterioration in the sensory quality of the produce.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following examples which are offered by way of illustration. The present invention is not limited to the examples given herein.

Materials and Methods

Unless stated otherwise in any given example provided herein, the following materials and methods were applied to study the iEWNS produced according to the instant disclosure.

The iEWNS were analyzed for their physical properties as well as their chemical composition. In more detail:

Particle number concentration and size distribution: The Scanning Mobility Particle Sizer (SMPS, TSI, Shoreview, Minn.) was employed for measuring the size and the particle concentration of the iEWNS. The sampling rate was maintained at 0.5 lpm (liters per minute). The arithmetic mean size was obtained from this distribution using the Aerosol Instrument Manager software (TSI, Shoreview, Minn.). Twenty discreet measurements were performed, each for duration of 120 seconds.

Electric charge: A Faraday Aerosol electrometer (Model 3068B, TSI, Shoreview, Minn.) was used to measure the aerosol current concurrently with the SMPS that measured the particle concentration. The sampling flow rate was 0.5 lpm for both instruments. Twenty discreet measurements were performed, each for duration of 120 seconds.

ROS characterization: The ROS content of each of the iEWNS was measured using the Trolox method as described in the art. Briefly, however, 5 mL of solution of Trolox (0.1 mM, in 0.05 M pH 7 phosphate buffer) was placed in an impinger (Midget Impinger, SKC Inc., Eighty Four Pa.) and connected to the output of the iEWNS generation system. The EWNS aerosol was bubbled through this solution for five minutes with a sampling rate of 0.5 lpm. Potential losses inside the impinger were calculated separately and taken into consideration. Two aliquots of 1 mL were taken from the impinger after the reaction time. The first aliquot was processed without further modification to detect the short-lived ROS, and the second aliquot was spiked with HRP (100 unit/mL final concentration) for the detection of $H_2O_2$.

Samples were incubated for 30 minutes at 37° C. prior to analysis as described previously.

Inactivation of bacteria and viruses inoculated on Stainless steel surfaces: FIG. 3 shows a three-needle (emitter) iEWNS synthesis and exposure setup, which was utilized for exposing microorganism inoculated stainless steel coupons (stainless steel coupons are used widely in food microbiology field for assessing the efficacy of antimicrobial technologies). The target surface was placed directly below the needle. The iEWNS were accelerated towards the inoculated coupons placed on top of the grounded electrode due to the electric field. During the exposure Temperature and Relative Humidity (T, RH) were recorded to ensure that all inactivation experiments were executed under the same conditions.

As control similarly inoculated surfaces were kept under same environmental conditions (Temperature and Relative Humidity) were monitored and recorded for each experiment.

Bacterial culture: The bacterial strains employed in this study were obtained from ATCC (Manassas, Va.). *Escherichia coli* (ATCC #25922), *Acinetobacter baumannii* (ATCC #19606), and *Listeria innocua* (ATCC #33090) were acquired were grown over night in Tryptic Soy Broth (Hardy Diagnostics, Santa Maria Calif.) inside a shaker incubator at 37° C. The overnight culture was then centrifuged at 300 rpm for five minutes. The pellet was re-suspended in DI water and the final concentration of the inoculum was adjusted to $10^8$ cfu/ml.

Inoculation Methodology: 10 µl of this bacterial inoculum was distributed on stainless steel coupons (stainless steel 304, diameter 1.82 cm, Stainless Supply, Monroe N.C.), by adding ten 1-µl droplets in a concentric manner near the center of the coupon. The effective concentration of bacteria on the coupons was $10^6$ cfu. The coupons were then placed inside a petri dish and the inoculum was allowed to dry, placed inside a biosafety cabinet. The treatment coupons were then removed from the petri dishes and utilized for experimentation, whilst the control coupons were placed in the same treatment chamber, away from the iEWNS generating needles, in order to determine the natural decay of the inoculated microorganisms.

Inoculum recovery and enumeration: Post-exposure control and exposed coupons were each added to a 50-ml micro-centrifuge tube containing 5 ml of 1× phosphate-buffered saline (VWR International, Radnor Pa.). The coupons were vortexed for 30 seconds and the resulting rinsate was utilized in a dilution plate counting assay.

Viral Culture: A suspension of influenza virus (A/PR/8/34 H1N1) (Virasource Inc., Durham N.C.) was used. A stock of $10^7$ Infectious Units/ml (IU/ml) of the virus was utilized for these experiments. The stock was thawed, divided into single-use portions, and stored at −80° C. until needed.

Inoculation Methodology: 10 µl of this viral stock solution was added to stainless steel coupons (stainless steel 304, diameter 1.82 cm, Stainless Supply, Monroe N.C.), by adding ten 1-µl droplets in a concentric manner near the center of the coupon. The effective concentration of virus on the coupons was $10^5$ IU. The coupons were then placed inside a petri dish and the inoculum was allowed to dry, placed inside a biosafety cabinet. The treatment coupons were then removed from the petri dishes and utilized for experimentation, whilst the control coupons were placed in the same treatment chamber, away from the iEWNS generating needles, in order to determine the natural decay of the inoculated virus.

Inoculum recovery and enumeration: The 50% Tissue culture Infective Dose ($TCID_{50}$) assay was used to quantify the viral inactivation. This is an endpoint dilution assay, which quantifies the amount of virus required to produce a Cytopathic Effect (CPE) in 50% of inoculated tissue culture cells. After treatment, the coupons were removed and washed in 2 ml of TPCK-DMEM (VWR International, Radnor Pa.) solution. 50 µl of this solution was re-suspended into 4.95 ml of infection media. Final concentration of the solution was $2.5 \times 10^4$ IU/ml. This was further diluted 1:1 in infection media. The solution was then added to the wells in serial dilution. The plates were incubated for 2 hours. The virus suspension was aspirated and replaced with 200 µl of infection media. The plates were further incubated for a minimum of two days. CPE was observed after three days. The $TCID_{50}$ score was obtained as the dilution at which 50% of the wells of the assay showed CPE. This value was then converted into the IU/ml value by utilizing the Spearman Kaerber Method.

Data analysis and statistics: Each experiment was repeated in triplicate. Each data point represents the arithmetic mean of three replicates. The standard deviation of the three trials was used as the error bars.

Log-reductions for coupon inoculation experiments were calculated for each treatment condition (control decay, each iEWNS treatment) according to the following equation where X(0) is the concentration of the bacteria at time=0 and X(t) is the concentration of bacteria recovered after time t of exposure.

$$\text{Log Reduction} = \text{Log}_{10}((X_{(t)})/(X_{(0)})) \quad (1)$$

Accounting for the natural decay of the microorganisms at time 't', the log reduction was calculated according to the following equation where, $X_{control}(t)$ is the microorganism concentration of the control coupon at time t while $X_{Exposed}(t)$ is the concentration of the exposed microorganisms at time t. The log reduction (LR) is defined as:

$$LR = \text{Log}_{10}((X_{Exposed(t)})/(X_{Exposed(0)})) \quad (2)$$

The Log Reduction as function of time was fitted with a linear equation as follows:

$$LR(t) = IR \times t \quad (3)$$

where IR (logs/min) is the Inactivation Rate and t is the time.

Biofilm generation: A 10% solution of Glucose was prepared in PBS. 5 ml of this 10% of glucose solution was added into 95 ml of Tryptic Soy Broth TSB medium to yield 0.5% (w/v) final concentration. 100 µl of overnight culture of *Acinetobacter baumannii* ATCC 19606 was added to this as the inoculum. The Stainless Steel coupons were cleaned and prepared as previously described. A stainless steel coupon Each coupon and 3 ml of inoculum were placed in individual wells of a 6-well plate. The plates were incubated on a gently shaking incubator at 37° C.

Biofilm exposure methodology: The inoculated coupons were removed from the 6-well plates; one coupon each was placed directly underneath an iEWNS emitter needle. Two distinct type of treatments were carried out. In the first case, 4 hours' post incubation, when the biofilms are expected to start adhering to the substrate, the coupons were removed from media, dried and placed directly underneath the iEWNS producing emitter.

Exposure was carried out for 30 minutes with h1EWNS. Post treatment, coupons were placed back into the media and incubated overnight. Another 30-minute treatment was carried out on these coupons 24 hours post initial incubation.

In second methodology of treatment, the biofilm was allowed to adhere for 24 hours post initial incubation. After which, the coupons were removed from media, dried and placed directly underneath the iEWNS producing emitter. Exposure was carried out for 30 minutes with h1EWNS. Post treatment, coupons were placed back into the media and incubated overnight. During h1EWNS treatment, control coupons were kept inside a petri dish in similar environmental conditions as the treatment.

Figure 12:
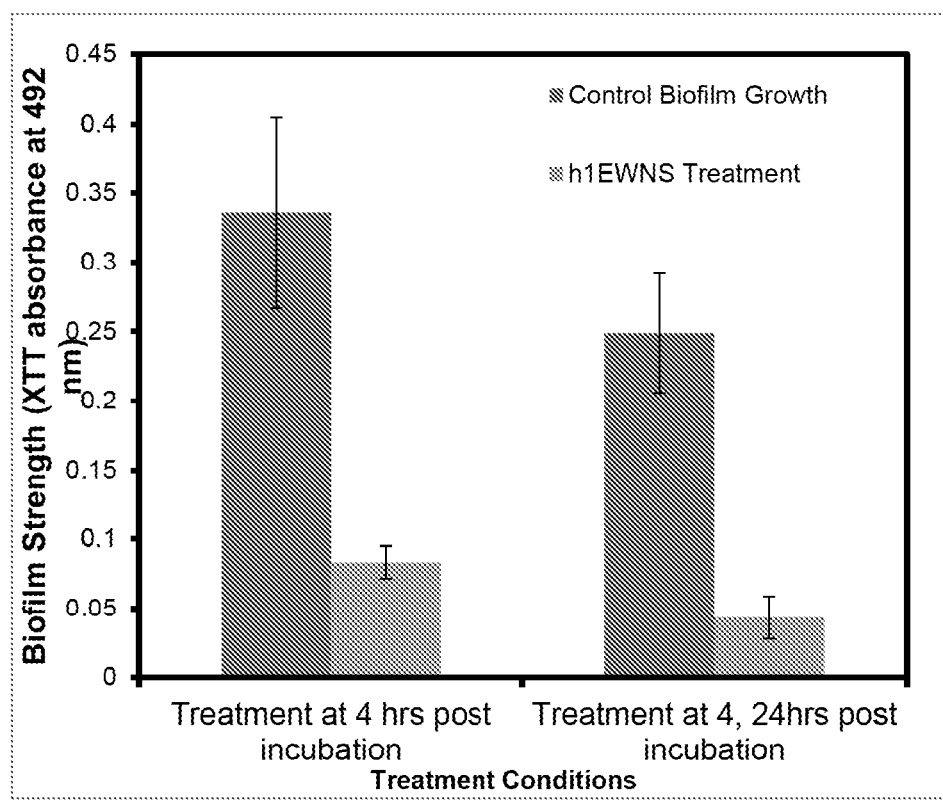
FIG. 12 is a plot showing the reduction in *A. baumannii* biofilm strength after h1EWNS treatment

Biofilm Enumeration: The method for the quantitative analysis of biofilms was the XTT assay. The XTT assay has been used to detect the biofilm formation and growth of various microorganisms. XTT is a tetrazolium salt that produces a water-soluble formazan product when it comes into contact with cellular respiration. This product was colorimetric ally quantified at 492 nm. The experiment was performed in triplicate. The results are shown in FIG. 12.

Design of Test Chamber to Study Airborne Viral Inactivation: To assess the inactivation of airborne H1N1, an aerosol test chamber (150-liter volume) was designed. Stainless steel was used to manufacture this chamber with multiple sampling ports on each lateral surface. This chamber was contained within a biosafety cabinet, in order to comply with safety regulations. See FIG. 13.

Figure 13:
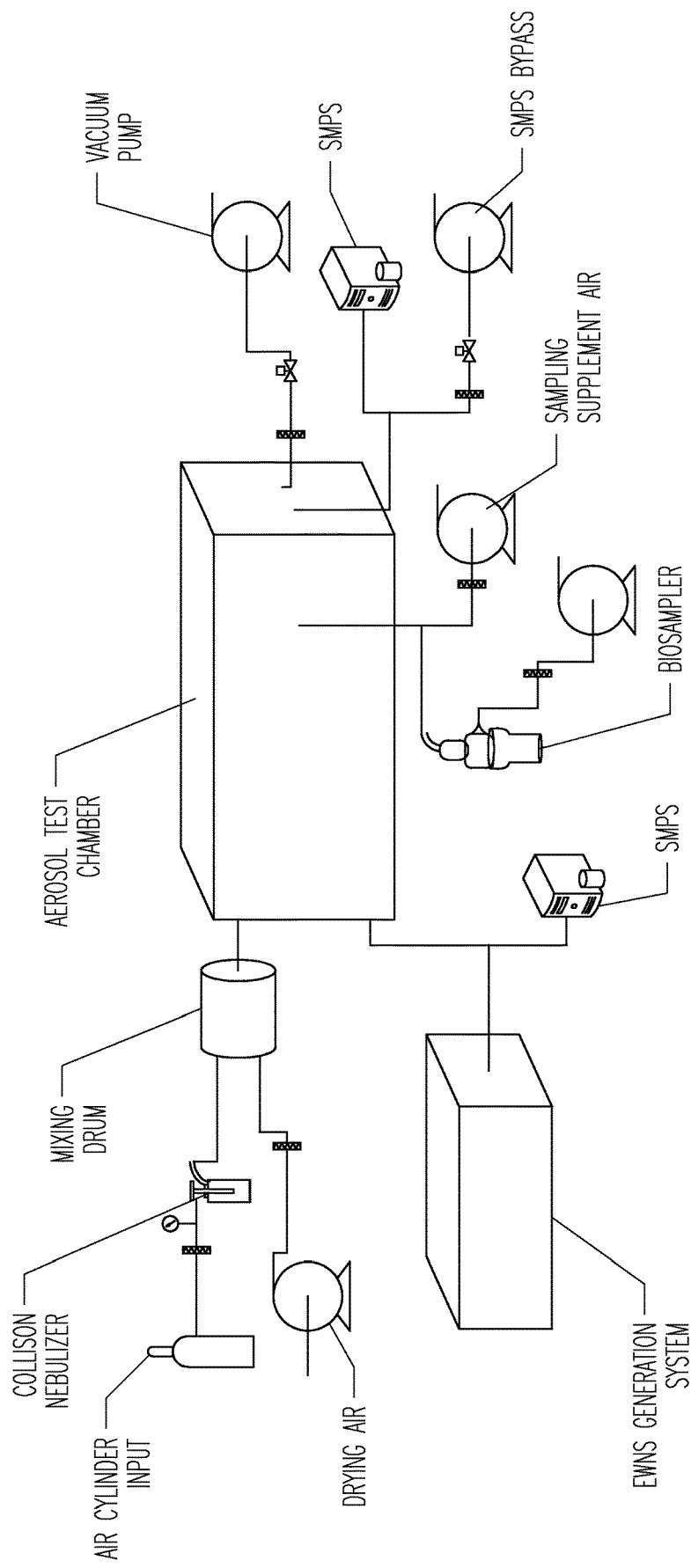
FIG. 13 is a schematic of a setup utilized for airborne flue inactivation experiments.

Viral bioaerosol production and sampling: The viral generation and sampling methods are detailed as follows:. Briefly, A single jet Collison containing 500 μL aliquot of 109 pfu/mL H1N1/PR/8 and 4.5 ml PBSA (PBS+0.1% Bovine Serum Albumin), was operated at 40 psi input pressure. The output of the nebulizer was mixed with dry air (3.3 lpm) and directed into a 150 liter stainless steel test chamber. Nine lpm of air was sampled from chamber using an SKC Biosampler (SKC Inc, Eighty Four, Pa.). An additional 3.5 lpm of HEPA filtered air was supplied to the Biosampler a supplementary air pump. The schematic of the experimental setup is as shown in the (FIG. 13). When sampling was not in progress equal volumes of air were bypassed through the sampler to an auxiliary pump. All exhaust points from the chamber were equipped with HEPA filters and contained within the biological safety cabinet.

Viral aerosol sample recovery and enumeration: The SKC Biosampler was utilized for sampling of the chamber airflow. 5 ml of Infection Media was added to the sampler as the collection medium. After sampling, this entire sample was used for analysis using the TCID50 assay. The sample was added to the wells of a 96 well plate in serial dilution. The plates were incubated for 2 hours. The virus suspension was aspirated and replaced with 200 μl of fresh infection media. The plates were further incubated for a minimum of two days. CPE was observed after three days. The 50% Tissue culture Infective Dose (TCID50) score was obtained as the dilution at which 50% of the wells of the assay showed CPE. This value was then converted into the IU/ml value by utilizing the Spearman Kerber Method.

Transmission Electron Microscopy (TEM) imaging for mechanism of inactivation: stainless steel coupons inoculated with the pathogens were treated for the time required for 5-logs removal (15 minutes for c1EWNS, five minutes for h1EWNS and l0.1EWNS, two minutes for c1h1EWNS). After treatment, the coupons were rinsed with phosphate-buffered saline (VWR International, Radnor Pa.). The recovered rinsate was further centrifuged at 300 rpm for five minutes and the resulting supernatant was removed and the pellet was used for fixation. A 2× solution of routine fixative (2.5% Glutaraldehyde 1.25%, Paraformaldehyde, and 0.03% picric acid in 0.1 M sodium cacodylate buffer (pH 7.4)) was added to the pellet in 1:1 manner. The pellet was fixed for at least two hours at room temperature in the above fixative, washed in 0.1M cacodylate buffer and post-fixed with 1% Osmium tetroxide ($OsO_4$)/1.5% Potassium ferrocyanide ($KFeCN_6$) for one hour, washed 2× in water and 1× in Maleate buffer (MB), and incubated in 1% uranyl acetate in MB for one hour followed by two washes in water and subsequent dehydration in grades of alcohol (10 minutes each; 50%, 70%, 90%, 2×10 minutes 100%). The samples were then put in propylene oxide for one hour and infiltrated ON in a 1:1 mixture of propylene oxide and TAAB Epon (Marivac Canada Inc. St. Laurent, Canada). The following day, the samples were embedded in TAAB Epon and polymerized at 60 degrees C. for 48 hours.

Ultrathin sections (about 60 nm) were cut on a Reichert Ultracut-S microtome, picked up onto copper grids stained with lead citrate, and examined in a JEOL 1200EX transmission electron microscope or a TecnaiG$^2$ Spirit BioTWIN and images were recorded with an AMT 2k CCD camera.

Example 1: EWNS Generation

The EWNS are synthesized via a combined electrospray and ionization, a method used to aerosolize particles and fibers from liquid suspensions according to the method described in Pyrgiotakis, G., et al., *Nanomedicine* 10: 1175-1183 (2014), which is incorporated by reference as if fully set forth herein. Electrospray relies on a strong electric field to aerosolize a liquid, which is contained in a fine metal capillary. The strong electric field causes the liquid to break into highly charged droplets. This phenomenon, known widely as Rayleigh effect, states that a liquid droplet with high surface charge density is unstable. The droplets continuously break down to the point where the surface charge is low enough to stop the continuous breaking of the droplets.

In brief, the generation of the EWNS is a combination of two phenomena, electrospray and ionization. In a typical experiment, a high voltage (in the kV range) is applied between a metal capillary that contains a liquid and a grounded counter electrode. The strong electric field between the two electrodes causes the formation of a conical meniscus at the outlet of the capillary, the so-called Taylor cone. From the tip of the Taylor cone, highly charged water droplets continue to break into smaller particles as they are drawn by the electrical field towards the counter electrode. These as-produced aerosols often show a remarkably narrow size distribution, which is considered to be monodispersed. At the same time, the high electric field causes some water molecules to split and can strip off electrons (ionization), resulting in a high number of reactive oxygen species (ROS). These particles hence produced are termed Engineered Water Nanostructures (EWNS). The "nano-carrier" platform presented in this case consists of utilizing the EWNS particles for the delivery of active ingredient (AI). In this method, a solution of an Active Ingredient (AI) is added to the EWNS generation bottle, in lieu of the de-ionized water put through the electrospray ionization process described above. The particles produced through this method are termed enhanced EWNS or iEWNS. These nano-scale particles contain both the active ingredient ('I') as well as the ROS produced and encapsulated in the particle during the electrospray ionization phase.

The lab-based, single needle, EWNS generation system allows the control of critical operational parameters such as the applied voltage (V), the distance between the needle and the counter electrode (d), the flow of the water (φ), in order to study the fundamentals of the EWNS synthesis and their formation mechanisms and properties (FIG. 2B). It was shown that by adjusting the electric field, flow of water and other critical operational parameters, EWNS properties (surface charge, size and ROS content) can be controlled and optimized. It was possible to fine-tune these operational conditions in order to optimize the EWNS properties and enhance their antimicrobial efficacy. In the current design, the flow of the water is controlled by adjusting the pressure inside the bottle, which provides better control and stability to the water flow compared to syringe type approaches. The flow can be further fine-tuned by controlling the relative height of the bottle to the needle that regulates the hydrostatic pressure that drives the flow (FIG. 2B). The metal needle is connected to a high voltage source and held over a grounded electrode. The distance between the needle and the counter electrode can be manually adjusted. A digital camera is used to monitor the cone formation and the proper operation of the generator. This design allows the integration of multiple needles (FIG. 3) by utilizing the same air flow and same voltage source, simply by fine-tuning the relative height of the water bottle to the needle. The EWNS can be sampled as aerosol for air disinfection applications or be delivered directly on the target surface that is located right underneath the needle $H_{hydr}$. Currently, each needle can generate an aerosol of approximately 50,000 #/cc at 0.5 L/min flow. It is worth noting that the single needle EWNS generator module consumes approximately 5 mW of power which is low enough to be powered by a battery.

Table 1 summarizes some of the active ingredients utilized to produce the iEWNS.

TABLE 1

| Active Ingredient (AI) | Concentration utilized (w/v) | Particle Nomenclature |
|---|---|---|
| Hydrogen peroxide | 1% | h1EWNS |
| Citric acid | 1% | C1EWNS |
| Lysozyme | 0.1% | L0.1EWNS |
| Combination | 1% (Hydrogen peroxide) + 1% (Citric acid) | c1h1EWNS |

Each AI solution was diluted in deionized water at concentrations not exceeding 1% w/v. Hydrogen peroxide, which is a known antimicrobial, is used in cellular processes and leaves no residue as it dissociates into water. A 1% w/v solution of $H_2O_2$ was utilized as the AI solution here. This concentration is approved by the FDA for processing various food processes such as starch bleaching. Another antibacterial used is citric acid, a major constituent of all citrus fruits, also a well-known antimicrobial, extensively used in food safety applications. A 1% w/v solution of citric acid was utilized in this study to produce the iEWNS, which is less than the concentration of citric acid found in lemons (5.75%). The use of antimicrobial enzymes, such as lysozyme, which is an enzyme found in egg white, tears, and breast milk, was also evaluated. Lysozyme is known to have antibacterial activity and was used in this study at a concentration of 0.1% w/v, which is comparable to the range of lysozyme concentration in human tears i.e. 750-3300 mg/L (0.075 to 0.330% w/v). A combination of hydrogen peroxide and citric acid, each at 1% w/v, was evaluated for testing potential synergistic effects from incorporating and delivering multiple AIs.

It should be noted that these concentrations of antimicrobials used in this study were exploratory and not optimized in order to increase antimicrobial potency. Other nature derived phyto-antimicrobials and enzymes/peptides and their combinations are expected to be developed and tested in future experiments.

Physico-Chemical Characterization of iEWNS

For all of the iEWNS synthesized in this study, their displayed sizes were in the nanoscale. The baseline EWNS generated using pure deionized water (no AI was used) were observed to have a mean diameter of 12.1 (±0.1) nm, in agreement with earlier studies with EWNS. The h1EWNS particles had the smallest size while the c1h1EWNS particles had the largest with an 11.9 (±0.3) nm and 48 (±3) nm mean diameter, respectively. The variation in size is attributed to the different pH and conductivity values of the starting aqueous solutions as these factors are known to affect the electrospray process.

Furthermore, the surface charge on the particles was measured using an aerosol electrometer. As with the size, the surface charge seems to be AI dependent. The highest surface charge was observed for the case of c1h1EWNS particles, while the least amount of charge was observed for the h1EWNS, with 77 (±14) $e^-$ and 11(±0) $e^-$ respectively. This surface charge is a very important property of the iEWNS. Others have shown that potential evaporation will increase the surface energy of the highly charged water droplets, thus bringing the charges closer, which is not a favorable process. This effectively retards the evaporation and the droplets reaches equilibrium at a terminal size. While not wishing to be bound by any specific theory, it is believed that this might be the reason behind the EWNS/iEWNS stability and lifespan. As it was shown in early studies with EWNS particles, the surface charge can result in long lifespan, reaching up to several hours in indoor environmental conditions.

It should be mentioned that, the link between size and charge imposes limitations in the way size is measured. The Scanning Mobility Particle Sizer (SMPS) utilized to measure iEWNS aerosol particle number concentration and size distribution underestimates the particle size. This is due to the fact that the SMPS instrument uses a Kr-85 neutralizer to bring particles towards the Boltzmann electric charge equilibrium (approximately +/−1 $e^-$ per particle). Therefore, by reducing the charge of the iEWNS particles, their size will be also impacted. In previous studies with baseline EWNS, the size was estimated with atomic force microscopy (AFM) and it was shown that their actual size was larger than the size measured by SMPS (actual size was almost double in size).

During the synthesis of the baseline EWNS particles, ROS are generated from aqueous phase and contained within the EWNS. It is known that ROS play an important role in the microorganism inactivation potential. For ROS quantification in the case of iEWNS nanoparticles, as described in detail in the methods section, the Trolox method was used, which estimates the ROS levels through the interaction of these iEWNS particles with Trolox, a vitamin E analog.

The results indicate that the various iEWNS produced in this study contained $10^{-6}$ to $10^{-8}$ nanomolar $H_2O_2$ equivalent levels of ROS/per particle. Further differentiation of these ROS into short lived (OH·, $O_2^-$) and long lived ($H_2O_2$) showed that the levels of short-lived ROS were highest in baseline EWNS, with no $H_2O_2$ detected in this case. The iEWNS generated here contained significantly lower quantities of short-lived ROS as compared base EWNS, but did contain $H_2O_2$. The highest levels of $H_2O_2$ were detected in h1EWNS, where $H_2O_2$ was used as AI in the starting aqueous solution.

In addition, for the cases of an organic AI, such as lysozyme and citric acid, the potential chemical transformation and chemical byproducts due to interactions from ROS present in the iEWNS particles and possibly from the electrospray/ionization process itself, were assessed using HPLC and UV/VIS absorption spectroscopy. In the case of lysozyme, no differences were observed between the standard stock lysozyme solution used in the synthesis and the lysozyme in the collected L0.1EWNS, which indicates no alterations in the lysozyme structure in this iEWNS. Similarly, no evidence of transformation or the formation of by-products of citric acid was observed in the case of c1EWNS and c1h1EWNS.

All of the iEWNS generated in this study were evaluated for their ability to inactivate *Escherichia Coli* 25922, a surrogate for *Escherichia coli* O157:H7 strain, which is a very common fecal contaminant of food and food surfaces, and responsible for many foodborne outbreaks. In addition, other types of microorganisms such as *Listeria innocua*, a surrogate for the pathogenic *Listeria Monocytogenes*, which is a gram-positive food related bacterium; *Acinetobacter baumannii* 19606, a bacterium that recently emerged as a major threat for nosocomial infections and Influenza H1N1/PR/8 virus (mouse adapted) were challenged with h1EWNS.

FIG. 9A illustrates the inactivation of the *E. coli* as a function of exposure time with the various iEWNS. Baseline EWNS (produced only with DI water) resulted in 2.4-log reduction after 45 minutes of exposure. For the c1EWNS, there was a 5-log removal observed after 15 minutes of treatment. Further increase in the antimicrobial inactivation rate was observed for h1EWNS, with 5-log reduction in 5 minutes. L0.1EWNS produced 5-log reductions at similar inactivation rates as the h1EWNS. Finally, the c1h1EWNS produced 5-log reduction in just two minutes of treatment, at a rate that is greater than the inactivation rates of hydrogen peroxide and citric acid combined, indicating synergistic effects between the AIs used.

For the gram-positive *Listeria innocua* (FIG. 9B), 5-log reduction was achieved in 15 minutes. Since the hydrogen peroxide eventually will become water and oxygen and will not leave behind any toxic by-products, these results are promising for the treatment of delicate food items (such as, but not limited to, berries, including raspberries, blackberries, and blueberries). In comparison, a study utilizing 10% w/v hydrogen peroxide solution for producing vaporized hydrogen peroxide could only produce 3 log reduction in concentration of *Listeria* on lettuce.

Figure 9D:
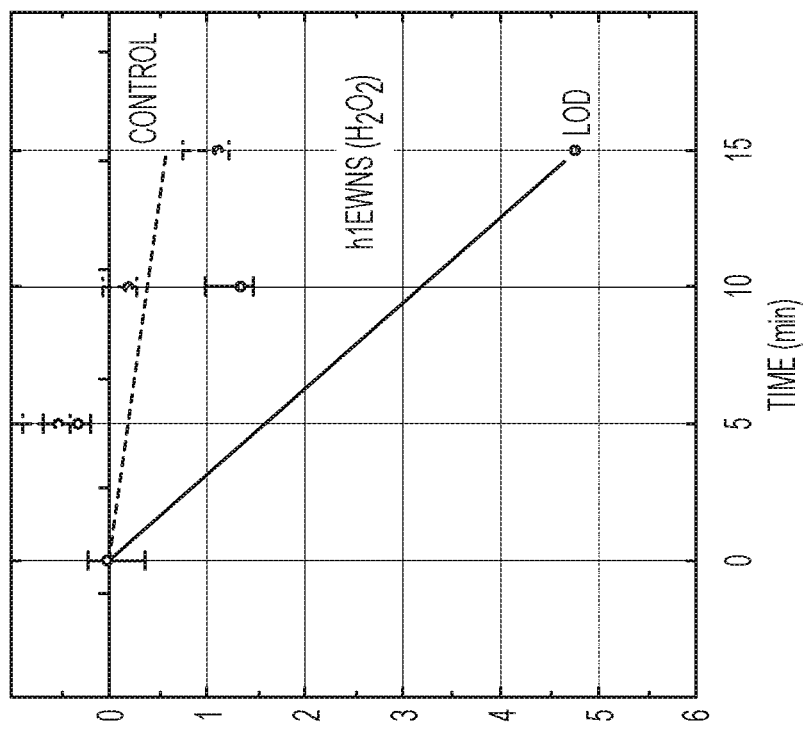
Figure 9C:
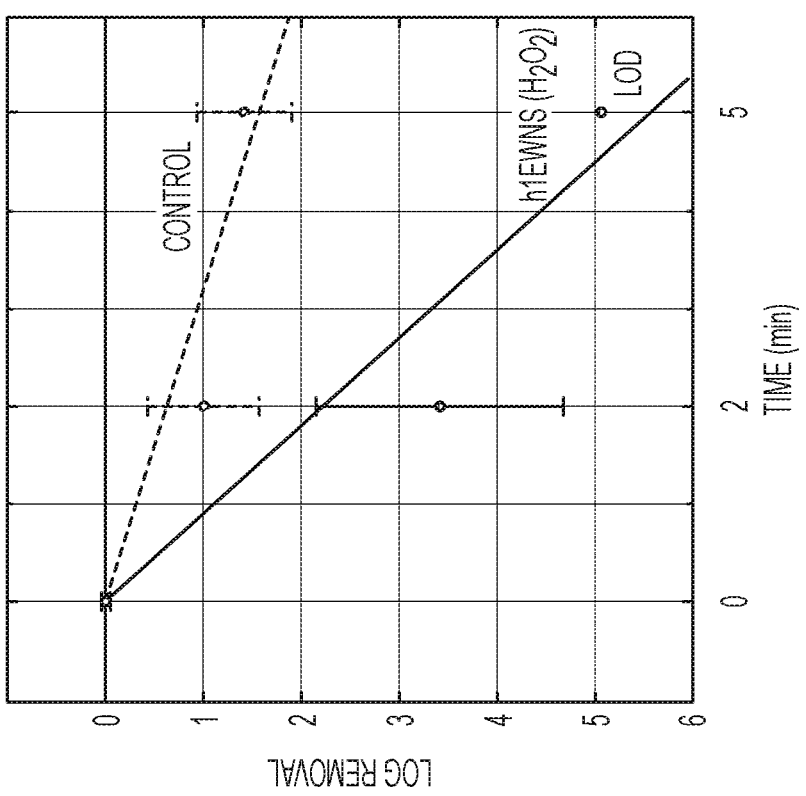
Figure 11A:
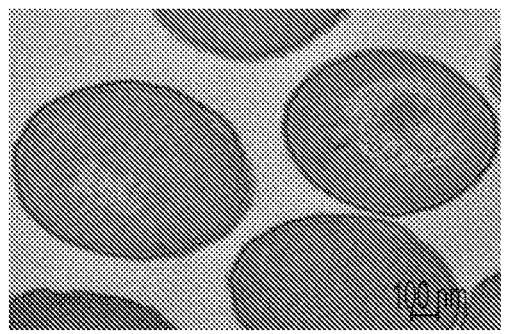
FIG. 11A-11E are transmission electron micrograph of *E. coli* treated with various iEWNS described herein. (a) Control, (b) H2O2, (c) citric acid, (d) lysozyme (e) Citric Acid and H2O2.
Figure 11B:
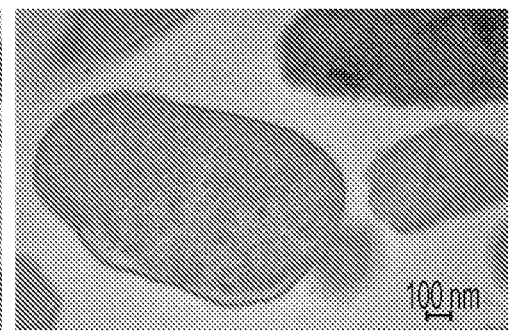
Figure 11C:
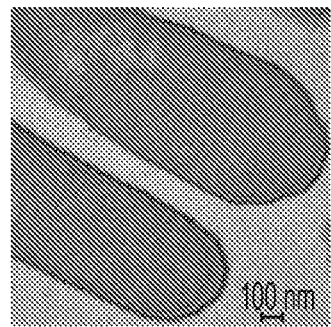
Figure 11D:
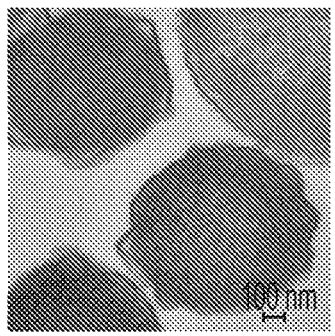
Figure 11E:
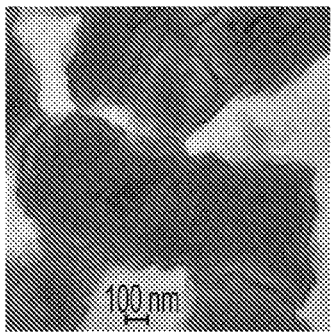

For the nosocomial infection causing *Acinetobacter baumannii*, the results indicate a 5-log reduction after 5 minutes of exposure (FIG. 9C). Studies have commented on the proliferation of this microorganism in the clinical setting and there is a major challenge in inactivating it effectively. Others have reported 4-log reductions in the concentration of *Acinetobacter* on surfaces using vaporized hydrogen peroxide (VHP), although the peak hydrogen peroxide concentration in those cases was extremely high (500-600 ppm). Here, the delivery of the h1EWNS in nanogram-level dose, as described herein, to achieve similar inactivation would make it an attractive technology for use in hospital room disinfection.

Finally, the efficacy of the h1EWNS as an antiviral treatment was assessed with the influenza H1N1/PR/8 virus. The h1EWNS was able to produce a 5-log reduction in the concentration of virus in 15 minutes of treatment (FIG. 9D). The dose per treated area delivered to the coupons was also in the nanogram range. In comparison, there have not been many studies that detail the effects of very low (<100 ppm) concentration of $H_2O_2$ on surface microorganism disinfection. Others have reported similar inactivation levels of surface deposited influenza, although it should be noted that the vapor phase hydrogen peroxide concentration in this case was about 1200 ppm and an exposure time close to 30 minutes. Similarly, in another study, 90 ppm of vapor phase $H_2O_2$ was required in order to achieve 5-log reductions in similar times of treatment.

Figure 10:
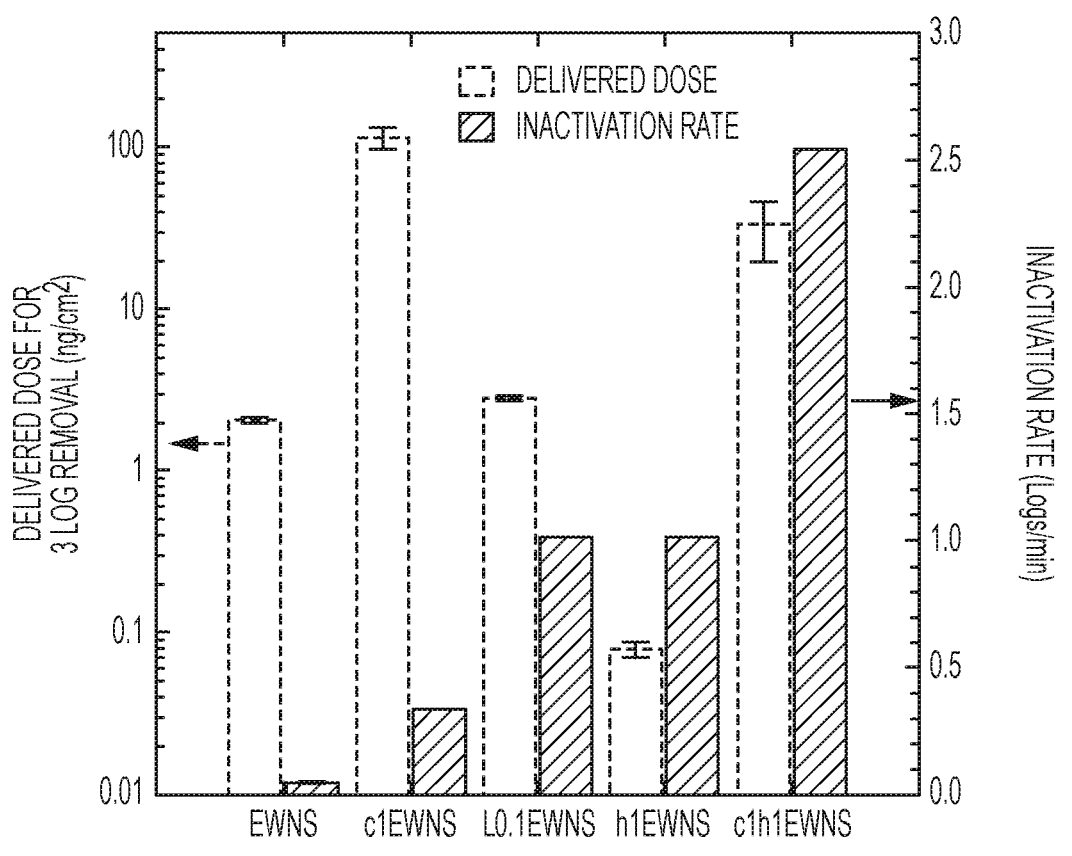

FIG. 10 illustrates the inactivation rates of these iEWNS against *E. coli*, as well as the delivered dose of each AI required to achieve a 3-log reduction. The effectiveness of individual iEWNS was analyzed using the following parameters, the inactivation rate (logs/min) and the dose required for the inactivation of 3-log of bacteria, a value that is commonly used to compare effectiveness.

The dose required for the inactivation of 3-log of bacteria was normalized to the surface area of microbial inoculum (Surface Normalized Dose, SND) and expressed as $g/cm^2$ This was done to account for the spread of the electrospray plume. For the baseline EWNS, the delivered dose per treated area required to produce 3-log reduction was 2.0625 $ng/cm^2$ at an inactivation rate of 0.05 logs/min. The most effective of the iEWNS, in terms of delivered mass dose was the h1EWNS with a value of 0.078 $ng/cm^2$ (at an inactivation rate of 1.05 logs/min). This is in sharp contrast to conventional treatments used in various applications, where studies with vaporized hydrogen peroxide have utilized high concentrations of hydrogen peroxide, in the range of 3-35% (weight by volume %) to achieve similar inactivation of microorganisms such as *Mycobacterium* on surfaces. It is worth mentioning that even higher concentration of $H_2O_2$ (5% w/v) delivered in a "wet" approach was found ineffective against pathogens on surfaces, whereas using only 1% w/v concentrations here using the h1EWNS particles were deemed highly effective.

In the case of the L0.1EWNS, the dose per treated area required to produce the 3-log reduction was assessed to be 2.81 $ng/cm^2$ at an inactivation rate of 1.05 logs/min. The efficacy of such minuscule dose of lysozyme is an indication that such enzymes with known antimicrobial activity can be delivered effectively through the iEWNS "nano-carrier" delivery approach, opening up an array of possibility to target specific microorganisms with very low quantities of other nature-inspired enzymes and peptides of known antimicrobial properties.

Similarly, the c1EWNS were also found extremely potent and a dose per treated area of 114.53 $ng/cm^2$ was enough to produce a 3-log reduction, at an inactivation rate of 0.35 logs/min.

In the case of combining citric acid and $H_2O_2$, c1h1EWNS, it was shown that the required dose per treated area to produce a 3-log reduction was 32.79 $ng/cm^2$, producing inactivation at an fast rate of 2.5 logs/min. While not wishing to be bound by any specific theory, this could be attributed to synergistic effects from combining the two AIs. The c1h1EWNS contain a combination of three AIs, citric acid, $H_2O_2$, and ROS generated from aqueous phase, making these nanoparticles highly potent. Such results are highly encouraging and illustrate that the iEWNS platform can be utilized to deliver a combination of AIs with each one suitable to target specific mechanisms and families of microorganisms on surfaces.

Collectively, the aforementioned inactivation results show that a minuscule dose per exposed area delivered using the iEWNS "nano-carrier" platform can be effective and result in complete inactivation in minutes, whereas, in wet approaches, gram-level quantities will end up on the surface of interest for the same or lower levels of inactivation (ng vs. g respectively). While not wishing to be bound by any specific theory, this can be attributed to the targeted, aerosol delivery of the AI utilizing the nanoscale features (extensive surface-per-volume area and high diffusivity) of iEWNS nanoparticles and the synergistic effects of the AIs incorporation with the ROS generated from aqueous phase in the EWNS. The minuscule quantities delivered on surfaces of interest, can minimize the risk from chemical residues and eliminate the production of chemical waste, while in the case of food pathogens, will reduce or even eliminate any sensory effects.

One significant feature of the iEWNS "platform" described in this disclosure is the minuscule dose of AI delivered to the target surface. To illustrate this, the dose required for 3-log bacterial removal was estimated based on the acquired data. FIG. 10 illustrates the required delivered dose to achieve a 3-log reduction for each iEWNS nanosanitizer.

For the baseline EWNS that contain no AI, the delivered dose of iEWNS aerosol per treated area required to produce a 3-log reduction was 2.0625 ng/cm$^2$ of iEWNS mass. The c1EWNS required 114.53 ng/cm$^2$ of iEWNS mass to produce a 3-log reduction, which translates to approximately 11.5 ng/cm$^2$ of citric acid delivered.

In the case of the L0.1EWNS, the dose per treated area required to produce the 3-log reduction was estimated to be 2.81 ng/cm$^2$ of iEWNS mass or to inactivate *E. coli* less than 0.3 ng/cm$^2$ of AI, which is significantly lower than what is in a tear drop. The efficacy of such minuscule dose of lysozyme delivered to the target surface area is an indication that such enzymes with known antimicrobial activity can be delivered effectively through the iEWNS-targeted delivery approach, opening up an array of possibilities to target specific microorganisms with very low quantities of other nature-inspired enzymes and peptides of known antimicrobial properties.

For h1EWNS, the delivered dose was 0.078 ng/cm$^2$ of iEWNS mass, which translates to 8 pg/cm$^2$ of AI. This is in sharp contrast to conventional treatments with aqueous solution of hydrogen peroxide at 5% and 10% concentrations that resulted in 2.2- and 3.5-log reduction respectively in the same amount of time.

For the citric acid and $H_2O_2$ combination (c1h1EWNS), it was shown that the required dose per treated area to produce a 3-log reduction was 32.79 ng/cm$^2$. This translates approximately to 1.6 ng/cm$^2$ for each AI. This synergistic additive effect is in agreement with results from studies using the combination of the two AIs in 'wet' type of treatments where the produce typically are dunked and tumbled in large pools of AI solutions. Such results are highly encouraging and illustrate that the iEWNS carrier platform can be utilized to deliver a combination of AIs with each one suitable to target specific mechanisms and families of microorganisms on surfaces.

Example 2: rEWNS with ROS Generated by Electrolysis of Deionized Water as AI

In some embodiments, ROS generated by electrolysis of deionized water (AI) is used instead of deionized water to generate the rEWNS of the various embodiments described herein. Electrolysis of deionized water can be used to pre-generate the ROS in solution (AI). It is worth noting that similar approaches have been used in the form of electrolyzed water to treat in a wet manner fresh produce such as lettuce, bell peppers and cucumber. Huang Y-R, et al., *Food Control* 19: 329-345 (2008), which is incorporated by reference as if fully set forth herein. However, such approaches involve the addition of salts (e.g., NaCl) and acids (e.g., acetic acid) to the water that leave behind a range of chemical residues that are not compatible with organic produce. Furthermore, the electrolyzed water approach is a "wet" method, and the fresh produce is either dipped in, or rinsed with electrolyzed water. Such wet methods can damage sensitive produce, such as berries, that cannot tolerate wet disinfection treatment, affecting sensory characteristics, leaving chemical residues and demanding large volumes of electrolyzed water, which increases the energy requirements.

ROS can be pre-generated in water using any known method for the electrolysis of water. In some examples, water (e.g., deionized water) is electrolyzed using a two-electrode assembly. The electrodes can be powered by a high-voltage DC power supply (e.g., at 600 V DC). Current is drawn through the water using a suitable current (e.g., current ranging from about 0.2 A to about 1.7 A). Such current will introduce chemical alteration in the water structure and create ROS. The chemical composition and ROS content of the electrolyzed water and the resulting rEWNS can be parametrically investigated with Electron Paramagnetic Resonance (EPR) and Trolox Equivalent Antioxidant Capacity (TEAC) methods, as a function of the applied voltage and electrolysis time. The electrospray and ionization that takes place during the rEWNS synthesis will further increase the ROS content and other properties of rEWNS and therefore, increase their potency.

Example 3: Production of hEWNS, Encapsulating Hydrogen Peroxide (AI)

Hydrogen Peroxide ($H_2O_2$) has been known for over a century for its germicidal properties. Varying $H_2O_2$ solutions has been demonstrated to be an effective disinfection agent on temperature sensitive surfaces, medical equipment, packing material, etc. Further $H_2O_2$ is on the FDA list for approved disinfecting agents allowed to be used with organic produce. Recently, there have been studies related to the treatment of produce by $H_2O_2$ for reducing microbial contamination. However, most of these studies involve wet methods, in other words, dipping or washing of produce with a $H_2O_2$ solution. Since the 1980s, $H_2O_2$ in vapor and mist form has also been used for disinfection of inanimate surfaces, entire rooms and produce surfaces.

For this example, commercially available solution of food grade $H_2O_2$ (3% w/v) is used. This solution is diluted in deionized water to the appropriate concentrations on the day of the experiment. This aqueous solution is utilized in, e.g., the EWNS generation setups shown in FIGS. 1B, 2A-2C, and 3, for producing the hEWNS.

Two concentrations of $H_2O_2$ were utilized for these studies, viz., 0.3% and 1%. These solutions are added to a tightly closed bottle that is connected to a stainless-steel needle (metal capillary) generating the EWNS particles, as described herein. The hEWNS produced with these solutions, termed h0.3EWNS and h1EWNS respectively, were utilized for microbial inactivation studies.

Example 4: Production of cEWNS, Comprising Citric Acid

A natural antimicrobial ingredient that is widely used in the food industry is citric acid. Citric acid has been demonstrated to be effective against a variety of food-related pathogens on produce when applied by the wet methods of dipping and washing. Commercially available citric acid powder was diluted to appropriate concentrations in deionized water. Two concentrations of citric acid were utilized for inactivation studies, viz., 0.5%, and 1%. The cEWNS thus produced are termed c0.5EWNSand c1EWNS respectively and were utilized for microbial inactivation studies.

Example 5: Production of LEWNS, Comprising Lysozyme

Lysozyme, which is a natural enzyme that is found in egg white, tears, and breast milk was investigated as an AI for EWNS. Commercially available Lysozyme was diluted to produce 0.1% w/v solution. This concentration of lysozyme was utilized for inactivation studies. The LEWNS thus produced was termed L0.1EWNS and was utilized for microbial inactivation studies.

Example 6: Evaluation of the Antimicrobial Efficacy of iEWNS (a.k.a. Enhanced EWNS) (e.g., rEWNS, hEWNS, and cEWNS) Using Stainless Steel Coupons The efficiency of the enhanced iEWNS (e.g., rEWNS, hEWNS, cEWNS) was assessed with microbial inoculation experiments on stainless steel coupons (SSC). A fecal indicator: $E.\ coli$, was used for inactivation studies. 10 μL of a $10^8$ cfu/ml inoculum of $E.\ coli$ were inoculated onto the surface of SSC by adding 10 μL droplets in a concentric fashion near the center. The coupons were dried in a biosafety cabinet (approx. 30 min). Following which, one coupon of each was placed underneath each capillary as shown in FIG. 3. The iEWNS particles were directed towards the coupons with the vertical electric field (E), as shown in FIG. 3. Control coupons were held in the same chamber, but away from the capillaries, under the same conditions of temperature and relative humidity. Multiple time point treatments were evaluated at 2, 5, 10, 15 and 45-minute exposure to produce inactivation curves. After treatment, coupons were added to centrifuge tubes containing Phosphate Buffered Saline (PBS) and vortexed for 30 sec to recover the surviving microorganisms. The resulting rinsate was dilution plated on TSA agar for enumeration of survivor $E.\ coli$ followed by incubation, colony counting and calculation of log reductions.

Figure 4:
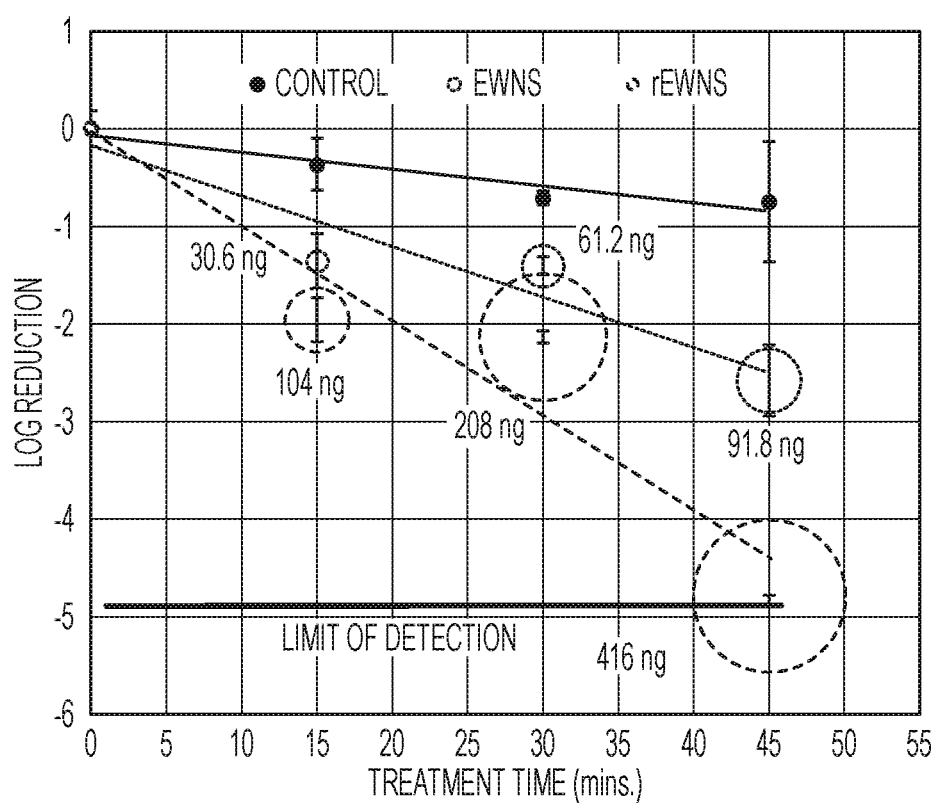
FIG. 4 is a plot of inactivation produced with rEWNS in *E. coli* inoculated on a stainless steel coupon, comparing the control to EWNS generated with only de-ionized water (basic EWNS) and rEWNS generated with water comprising ROS produced using electrolysis of water as AI. The size of the circles represents the delivered dose.

In the case of ROS pre-generated through electrolysis of water as an AI to be encapsulated, the particles were termed as rEWNS and the results of the $E.\ coli$ inactivation produced by rEWNS is shown in FIG. 4. The results indicate inactivation below the detection limit (4 logs compared to controls) after 45-minute treatment. This inactivation was compared with the EWNS particles, produced with only DI water, which resulted in only 1.9 logs reduction compared to controls. This represents a 2-fold increase in the inactivation produce. It is worth noting that the total dose of the ROS delivered to the $E.\ coli$ was in nanogram levels, with a maximum being 416 ng at 45 minute exposure.

Figure 5:
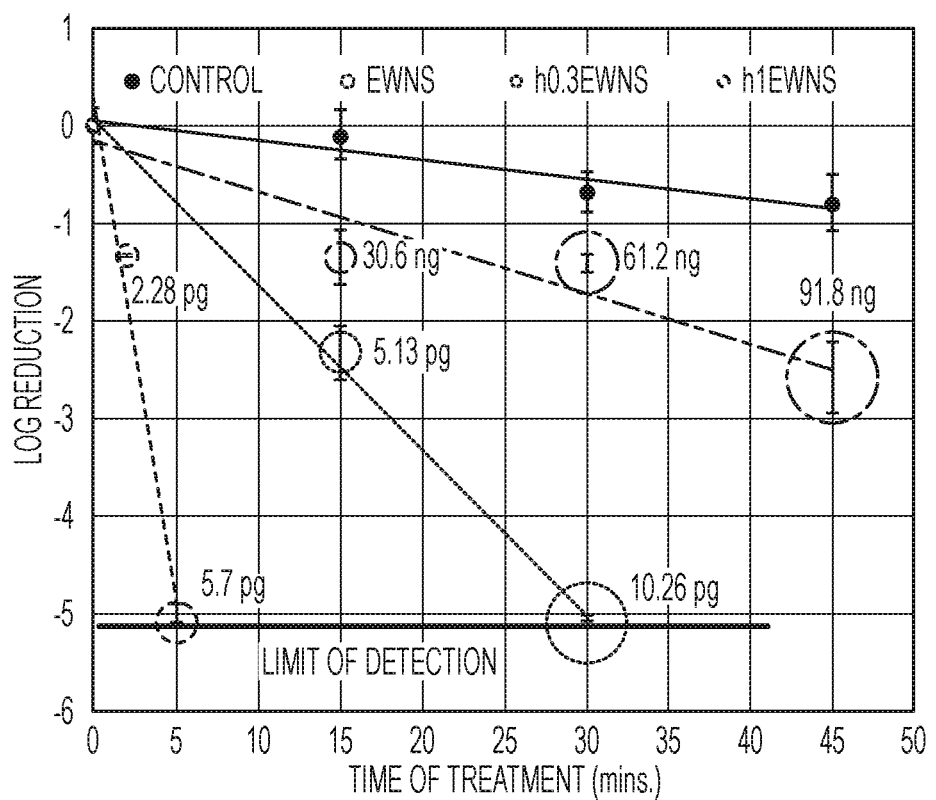
FIG. 5 is a plot of inactivation produced with hEWNS in *E. coli* inoculated on a stainless steel coupon, comparing the control to EWNS generated with only de-ionized water and hEWNS generated with water comprising $H_2O_2$ as AI at two different concentrations. The size of the circles represents the delivered dose.

In the case of hEWNS the results are shown in FIG. 5. Two types of particles evaluated. The h0.3EWNS, produced with 0.3% c, resulted in $E.\ coli$ inactivation that reached detection limit (4.3 logs when compared to controls) after 30 mins exposure. For comparison, at 30 minutes, the EWNS produced with only DI water displayed only 1.4 logs reduction. This represents a 3-fold increase for the h0.3EWNS over EWNS. An intermediate data point at 15 mins treatment was evaluated to establish a trend. It is worth noting that he total dose of $H_2O_2$ delivered to the $E.\ coli$ was 10.26 picograms after 30 minutes of exposure. The h1EWNS particles, produced with 1% $H_2O_2$ displayed a significant increase in inactivation. The inactivation of $E.\ coli$ was complete, below limit of detection (5 logs compared to controls) in just 5 minutes of exposure. This represented only the minute dose quantity of 5.7 picograms. The 2-minute treatment data point was also evaluated to establish a trend.

Example 7: Evaluation of the Scale Up, Targeted and Precision Delivery Platform Against Inoculated Foodborne Contaminants and Natural Microbiota on Surface of Berries The antimicrobial efficacy of the enhanced EWNS synthesized from a. ROS produced by electrolysis, b. 0.5%, 1% $H_2O_2$ and 2% $H_2O_2$ and c. 0.5, 1% citric and 2% citric acid against a selective set of foodborne contaminants of interest to the food industry including two bacteria ($E.\ coli$—fecal indicator and $Listeria\ innocua$—surrogate to $L.\ monocytogenes$ and an environmental contaminant), a filamentous fungus ($Botrytis\ cinerea$) and a non-cellular microbial structure (bacteriophage MS2-surrogate to viruses). Inoculation experiments are performed on two types of fresh berries (blackberries, and raspberries), a delicate fresh produce category that can be an ideal candidate for disinfection with the "dry", green iEWNS platform. In addition to the inoculation experiments, the potential of the enhanced EWNS to inactivate native microflora on berries is also be assessed. Finally, the possible extension of shelf life of exposed fresh berries and a sensory evaluation is done to complete the assessment portfolio.

Products sensitive to conventional disinfection methods, such as organic and conventional fresh berries (blackberries) are included in the evaluation experiments. They are purchased from local groceries or provided by distributors. The samples are carefully selected to be in good condition (no cuts, bruises, injuries, signs of spoilage) and similar in size, maturity and color. In earlier inoculation studies with tomatoes, rinsing with soap solution and DI water was used to remove the natural flora. However, due to the sensitive nature of the berries a modified protocol of using a 20 min UV irradiation followed by a 2 minutes alcohol dip is employed. Preliminary data show that this method is equally effective.

The panel of microorganisms to be evaluated for inoculation experiments includes: Bacteria: $E.\ coli$ (ATCC #25922), $Listeria\ innocua$ (ATCC #33090), Fungus: $Botrytis\ cinerea$ (ATCC #11542) and Virus: Bacteriophage MS2 (DSM 13767).

Figure 8A:
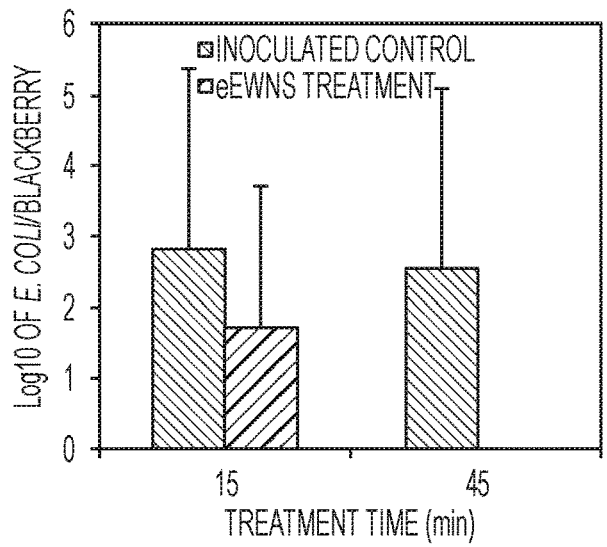
FIGS. 8A-8C are bar graphs of cfu reduction as a function of time for blackberries treated with rEWNS (with ROS generated by electrolysis of deionized water as AI): (A) Inactivation of *E. coli* inoculated on blackberries. (B) Inactivation of Total Viable Microorganisms; (C) Inactivation of Yeasts and Molds.
Figure 8B:
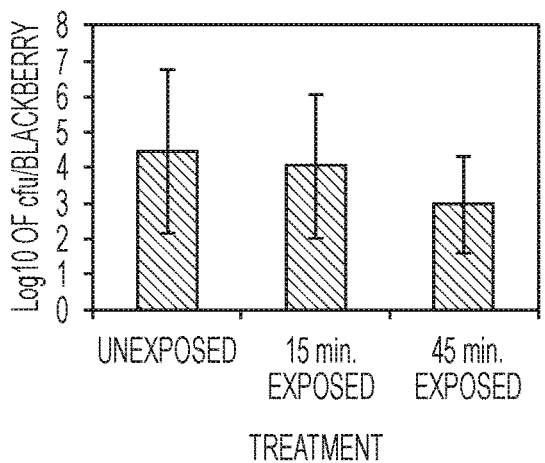
Figure 8C:
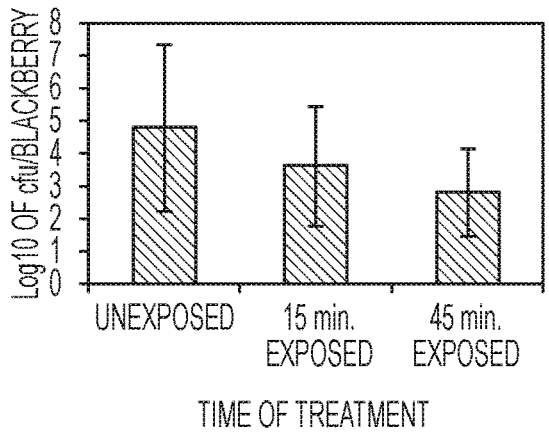

The targeted delivery of the iEWNS aerosol is performed using the electric field generating the iEWNS (FIG. 3) and the iEWNS aerosol is targeted towards the surface. As controls, inoculated but not exposed to iEWNS coupons is held away from the EWNS generator but at same exact conditions (relative humidity, temperature, ozone etc.). During the exposure, the EWNS concentration, relative humidity (RH), temperature and ozone levels are monitored The berries are inoculated according to our established protocols and exposed for specific periods of time (15 and 45 min) in order to get a dose response relationship for each type of organism. $E.\ coli$ (ATCC #25922) is prepared by re-suspending 1 mL of overnight culture in 1 mL of 1×PBS to yield a suspension with a final concentration of $10^8$ CFU /ml. Individual berries are spot inoculated with 10 spots of 1μl each, resulting in an inoculum of $10^6$ cfu. Botrytis (ATCC #11542) is grown on Potato Dextrose Agar (PDA) at RT for greater than 7-10 days until sporulation. Resulting fungal spores are harvested by adding 10 ml of sterilized aqueous solution of Tween 80 (00.5% v/v) to the surface culture. Berries are spot inoculated with spores of approximately $10^5$ spores/ml stock solution. Bacteriophage MS2 (DSM 13767) are grown using a double layer agar method utilizing the host bacteria *E. coli* K12Hfr (NCTC 12486). Berries are then spot inoculated with a virus inoculum of approximately $10^6$ PFU/ml stock solutions. As controls, spot inoculated berries are left in a control chamber, with same environmental conditions as exposed ones but without exposure to rEWNS. Pre and post exposure, the inoculated berries are analyzed microbiologically to quantify microorganisms present. The results are shown in FIGS. 8A-8C. In separate experiments, the mechanism of inactivation is confirmed using Transmission Electron Microscope. Fresh produce including berries can harbor large and diverse microbial populations, including indigenous flora, human enteric pathogens and spoilage microbes, depending on the type of produce, irrigation water, farming practices, and storage conditions. These are referred to as "naturally occurring flora" as they are not spot inoculated on the surface of the fruit. In this part of the experiment, the effect of enhanced EWNS on these "naturally" present and diverse microbial communities are assessed through two fundamental parameters: total viable count and yeast/mold count. Berries used are obtained from a local distribution center on the day of their arrival and are used for the experiments without any further processing. The berries are exposed for 15 and 45 minutes using rEWNS.

Following exposure, the berries are added to a sterile bag containing Maximum Recovery Diluent (MRD) and Serial dilutions are plated according to standard microbiological methods using Plate count agar (PCA) incubated at 30° C. for 72 h to determine total viable count and acidified Potato Dextrose agar (PDA) incubated at RT for 5-7 days for Yeast and Molds. The efficacy of EWNS to inactivate the 'naturally' present species are calculated by comparing the mean counts for each AI, with and without each rEWNS exposure. The log reduction in the concentration of the Total Viable Counts and Yeast plus Molds is shown in FIGS. 9B-C.

Fresh fruit such as berries are perishable items. The effect of i EWNS (rEWNS, hEWNS (0.3%, 1% and 2%) and cEWNS (0.5%, 1% and 2%) on shelf life extension and its impact on physical and sensory quality characteristics of the fruits are investigated. Berries grown under conventional and/or organic practices are obtained through collaboration with USDA-ARS's Beltsville Agricultural Research Center. The products are harvested and pre-cooled as per typical commercial handling protocol. Additional samples are supplemented with products obtained from local distribution centers during off-seasons.

The scale up EWNS lab-grade apparatus described in FIGS. 2A-2C, 3, and 4 is utilized. Produce samples are exposed to enhanced iEWNS and then stored at 5° C., a typical storage temperatures for these produce items. Control berries that had not undergone any treatment are used for comparative studies. Two treatment regimes are evaluated, a one-time, 1 hr iEWNS treatment in the beginning of storage, and in the second scenario, an additional intermittent iEWNs treatment for another 1 hr after the first day of storage. Treated and untreated fruit are monitored as follows.

Microbiological, physical, sensory and shelf life evaluation: Bioburden (TVC and Yeast and Molds), Physical characteristics (Color, tissue integrity and texture) and Sensory parameters are assessed before the EWNS treatment, immediately after the treatment and at intervals of two days, using instrumental, cultural and sensory techniques. Color is determined using a Minolta colorimeter, and the texture with a TA-XT2 Texture Analyzer. Tissue membrane integrity is assessed via conductivity of the electrolyte leakage. Decay indices is computed based on the decay intensity and the area of decay. Overall visual quality, freshness, discoloration, and off-odor is evaluated by an in-house sensory panel with trained sensory judges (note visual observation is exempted from IRB approval by HHS Exemption). USDA-ARS at Beltsville Md. has a state-of-the-art sensory evaluation facility and fully trained and experienced sensory judges. The facility has ten individually partitioned booths, fully equipped with computers and Sensory Software. Products are coded with random three-digit numbers to mask treatment identity and maximize evaluation objectivity. Panel selection will include balanced gender, age, ethnicity etc. Both structured and non-structured scales are used. Scores are collected and analyzed using Compusense software program.

Microbial changes in microbial profile after treatment and during storage will also be monitored using direct plating methods. Total aerobic bacteria, and yeast and mold are enumerated using TSA, and PDA-chloramphenicol, respectively as described herein.

Example 8: Evaluation of Mechanism of Inactivation

The mechanism of inactivation of the various iEWNS was qualitatively assessed by transmission electron microscopy (TEM) (FIG. 11, panels (a)-(e)). *E. coli* cells isolated from the control samples (not exposed) are shown in FIG. 11, panel (a). The definite shape and structure of the gram-negative cell membrane are seen. The h1EWNS treated *E. coli* cells (FIG. 11, panel (b)) showed rupture of the membrane and leakage of cellular components.

The c1EWNS treated *E. coli* (FIG. 11, panel (c)) showed mostly intact cell walls, indicating that the primary mechanism of action of the c1EWNS is not through membrane damage, but rather through intracellular process, such as interference with the respiratory chain of the bacterial cell.

c1h1EWNS-treated cells, where stretching and deformation of the cell membrane was observed with some leakage of the cellular components, indicative of potential synergistic effects (FIG. 11, panel (d)). While not wishing to be bound by any specific theory, it is believed that this might indicate that hydrogen peroxide is not producing complete peroxidation, but causes changes to the membrane permeability, thus facilitating the entry of the citric acid into the cell to complete the inactivation.

The L0.1EWNS-treated *E. coli* cells are indicative of lysis and loss of their cellular shape (FIG. 11, panel (e)). This membrane effect has been observed in earlier studies related to the effect of lysozyme on microorganisms such as *E. coli* and *Pseudomonas*. The complete hydrolysis of peptidoglycans in the cell membrane has been implicated as the major inactivation mechanism for lysozyme.

Figure 6:
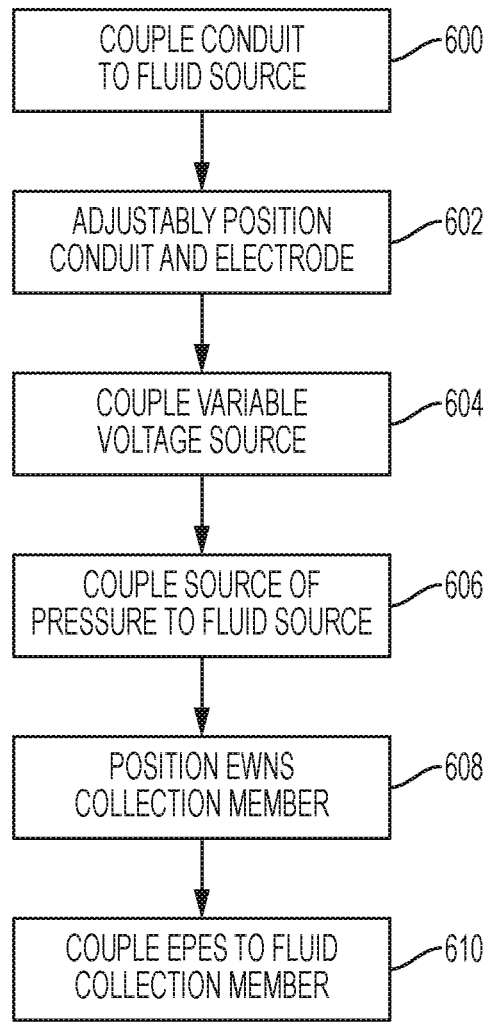
FIG. 6 is a flowchart for making a system used for making and using iEWNS.
Figure 7A:
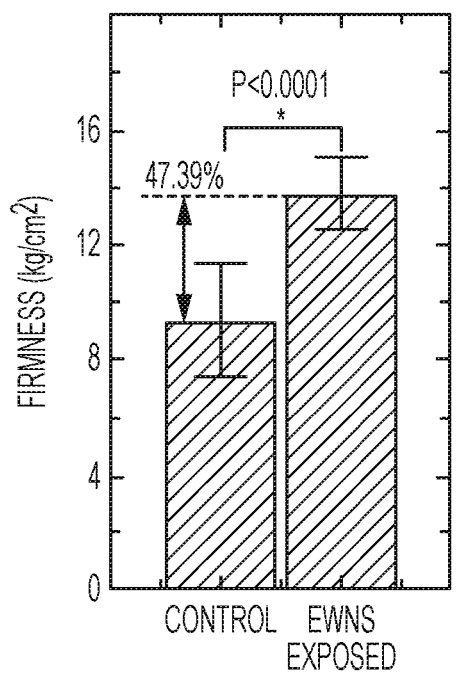
FIGS. 7A-7D are bar graphs of sensory evaluation data of cherry tomatoes treated with iEWNS.
Figure 7B:
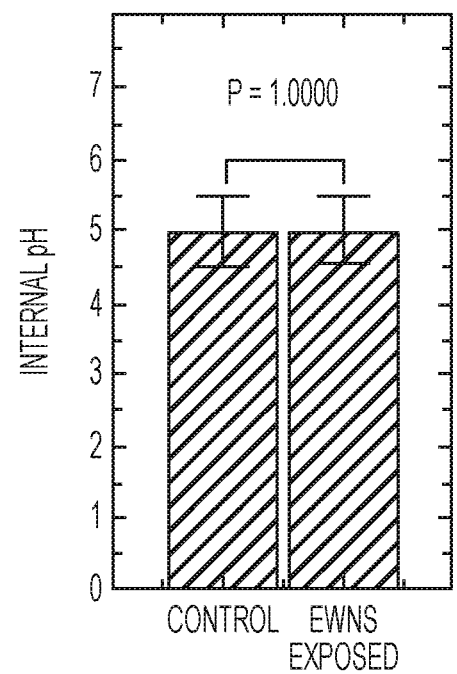
Figure 7C:
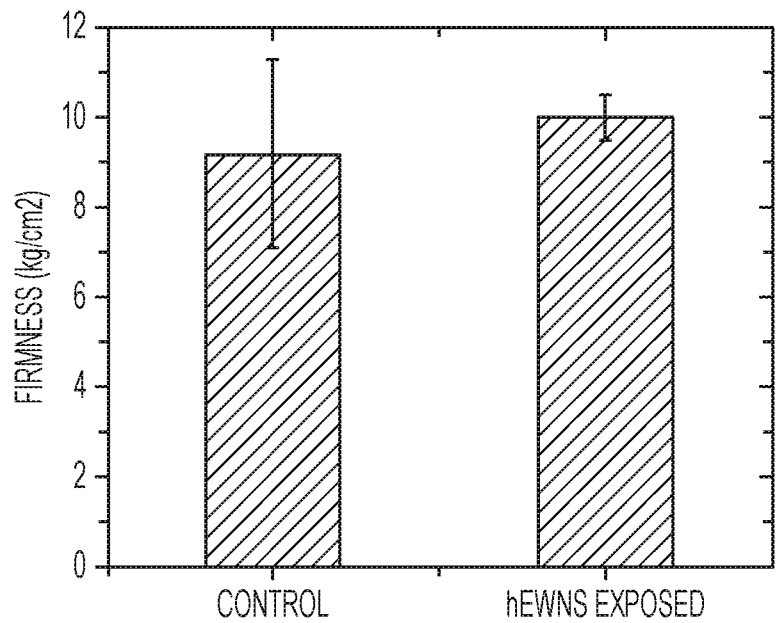
Figure 7D:
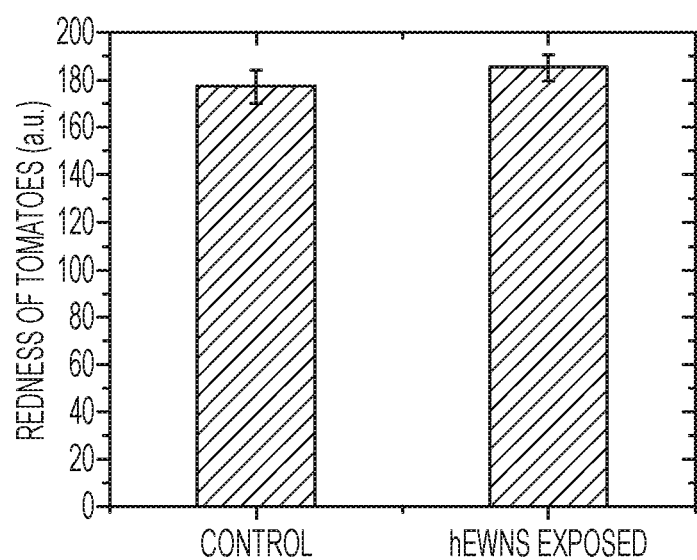

FIG. 6 is a flowchart for making the system 200, in an example embodiment.

At 600, a conduit is coupled to a fluid source configured to contain a fluid (e.g., deionized water, water comprising ROS produced using electrolysis of water, or water comprising an active ingredient, such as $H_2O_2$ and citric acid), the conduit forming an aperture.

At 602, the conduit is adjustably positioned with respect to an electrode to set a predetermined adjustable distance from the aperture to the electrode. In an example, adjustably positioning the conduit includes positioning the aperture is above and substantially along a vertical axis with respect to the electrode. In an example, at least some of the engineered water nanostructures fall onto the electrode. In an example, adjustably positioning the conduit is along the vertical axis to set the predetermined adjustable distance.

At 604, a variable voltage source is electrically coupled between the conduit and the electrode, the variable voltage source configured to impart an electric potential difference between the conduit and the electrode. Fluid from the fluid source that passes through conduit and the aperture is changed to engineered water nanostructures upon coming into proximity of the electrode based on the predetermined distance and the electric potential. In an example, the electrode forms an electrode aperture and wherein the engineered water nanostructures come into proximity of the electrode by passing through the electrode aperture. In an example, the conduit is formed of an electrically conductive material, the voltage source is coupled to the electrically conductive material, and the electric potential difference between the aperture and the electrode induces an electric field between the aperture and the electrode through which the fluid passes. In an example, the conduit is a metallic capillary. In an example, the metallic capillary has a first end and a second end opposite the first end, wherein the first end is coupled to the fluid source and the aperture is at the second end.

At 606, a source of pressure is coupled to the fluid source, the source of pressure configured to place fluid in the fluid source under pressure to force the fluid into the conduit.

At 608, an engineered water nanostructure collection member is positioned with respect to the electrode, wherein engineered water nanostructures that contact the electrode are collected by the engineered water nanostructure collection member.

At 610, an electrostatic precipitator exposure system is fluidly coupled to the fluid collection member, the electrostatic precipitator exposure system configured to apply engineered water nanostructure as collected by the fluid collection member to a target.

Additional embodiments relate to a method for inactivating at least one of viruses, bacteria, bacterial spores, and fungi on a substrate comprising: applying electrolyzed water engineered water nanostructures (EW-EWNS) comprising reactive oxygen species (ROS) and surface charge to the substrate to inactivate the at least one of viruses, bacteria, bacterial spores, and fungi.

Still other embodiments relate to a method for inactivating at least one of viruses, bacteria, bacterial spores, and fungi on a substrate comprising: applying engineered water nanostructures (EWNS) to the substrate to inactivate the at least one of viruses, bacteria, bacterial spores, and fungi; the EWNS comprising (i) reactive oxygen species (ROS), (ii) at least one active ingredient in addition to the ROS, and (iii) a surface charge.

Yet other embodiments relate to a system, comprising: a fluid source configured to contain an aqueous composition comprising at least one active ingredient; an electrode; a conduit, coupled to the fluid source and forming an aperture, wherein at least one of the conduit and the electrode are adjustably positionable with respect to one another to set a predetermined adjustable distance from the aperture to the electrode; and a variable voltage source, electrically coupled between the conduit and the electrode, configured to impart an electric potential difference between the conduit and the electrode; wherein fluid from the fluid source that passes through conduit and the aperture is changed to engineered water nanostructures upon coming into proximity of the electrode based on the predetermined distance and the electric potential, wherein the EWNS comprise the at least one active ingredient encapsulated therein.

Other embodiments relate to a method, comprising: coupling a conduit to a fluid source configured to contain at least one active ingredient, the conduit forming an aperture, adjustably positioning the conduit with respect to an electrode to set a predetermined adjustable distance from the aperture to the electrode; and electrically coupling a variable voltage source between the conduit and the electrode, the variable voltage source configured to impart an electric potential difference between the conduit and the electrode; wherein fluid from the fluid source that passes through conduit and the aperture is changed to electrolyzed water engineered water nanostructures upon coming into proximity of the electrode based on the predetermined distance and the electric potential.

Still other embodiments relate to (a) engineered water nanostructures (EWNS) comprising (i) reactive oxygen species (ROS), (ii) at least one active ingredient in addition to the ROS, and (iii) a surface charge; and (b) electrolyzed water engineered water nanostructures (EW-EWNS) comprising reactive oxygen species (ROS) and a surface charge.

Example 9: Inactivation of *Acinetobacter baumannii* Biofilms

The results of the biofilm treatment are shown in FIG. 12. The results indicate that there is significant reduction in the biofilm strength after treatment by h1EWNS. For both types of treatments, there was reduction observed in the signal at 492 nm. For treatment performed after 4 and 24 h, there was 76% reduction. Whereas for the treatment of more mature biofilm (24 h post incubation), there was 81% reduction. These results indicate that the h1EWNS is effective in treating surface biofilms at various stages of growth and maturation. In sum, the methods described herein can lead to a reduction in biofilm strength following treatment with the EWNS described herein, including h1EWNS, of at least 50%, at least 60%, at least 70%, at least 80%, at least 90%, or at least 99% or more; from about 50% to about 100%, about 50% to about 80%, about 60% to about 90%, or about 70% to about 95% at 4 h or 24 h post incubation.

Example 10: Inactivation of Airborne Influenza H1N1/PR/8

Figure 14:
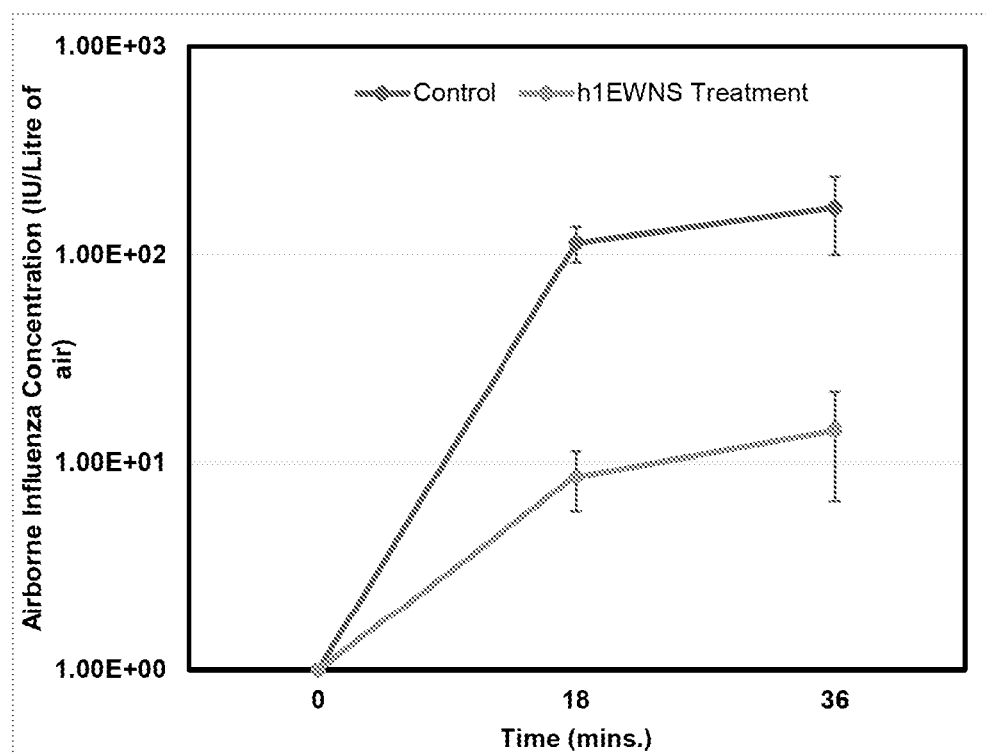
FIG. 14 is a plot showing the results of airborne inactivation of H1N1/PR/8 with h1EWNS.

The results of bioaerosol inactivation are as shown in FIG. 14. The negative controls and the h1EWNS treatment is shown in FIG. 14. For the controls, the first sample taken after 1 air exchange, at 18 minutes of nebulization, indicated an airborne Influenza H1N1/PR/8 concentration of 114.04 IU/Liter of air. After continued nebulization, the second sample was taken after 2 air exchanges, at 36-minute timepoint. This sample contained 167.81 IU/Liter of air of Influenza H1N1/PR/8.

For the h1EWNS treatment, the two samples were taken at the same timepoints. Here for the first timepoint, at 18 minutes, the concentration of airborne Influenza H1N1/PR/8 was observed to be 7.45 IU/Liter of air. This indicates a 94% reduction in the concentration. The second sample showed similar levels of inactivation. Here the h1EWNS treatment sample contained 11.63 IU/ Liter of air, which again represents a 94% reduction in concentration from the corresponding control sample. In sum, the methods described herein can lead to a reduction of the concentration of an influenza virus, such as H1N1/PR/8, in air following treatment with the EWNS described herein, including h1EWNS, of at least 50%, at least 60%, at least 70%, at least 80%, at least 90%, or at least 99% or more; from about 50% to about 100%, about 50% to about 80%, about 60% to about 90%, or about 70% to about 95%.

The inactivation results indicate that the h1EWNS technology is an effective tool for addressing the problem airborne transmission of viruses.

What is claimed is:

1. A method for inactivating at least one of viruses, bacteria, bacterial spores, fungi, and natural flora present on a substrate comprising:
    applying enhanced engineered water nanostructures (iEWNS) for a targeted and precise delivery to the substrate to inactivate the at least one of viruses, bacteria, bacterial spores, fungi and natural flora;
    the iEWNS comprising (i) reactive oxygen species (ROS), (ii) at least one active ingredient in addition to the ROS, and (iii) a surface charge, wherein the at least one active ingredient is present separate and in addition to any at least one active ingredient that is generated when the iEWNS are generated.

2. The method of claim 1, wherein the substrate is selected from the group consisting of a wound, skin, foodstuffs, surfaces and air.

3. The method of claim 1, wherein the active ingredient is an antimicrobial active ingredient.

4. The method of claim 3, wherein the antimicrobial active ingredient is at least one of hydrogen peroxide, one or more inorganic antimicrobials, one or more organic acids and salts thereof, one or more chemical antimicrobials, one or more ovo antimicrobials, one or more lacto antimicrobials, and one or more bacto antimicrobials, and one or more phyto antimicrobials, inorganic colloids, emulsions or combinations thereof.

5. The method of claim 1, wherein the bacteria are at least one of gram-positive and gram-negative bacteria.

6. The method of claim 1, wherein the bacteria comprise mycobacteria.

7. The method of claim 1, wherein the inactivation comprises reducing the number of colony forming units (cfu) on the substrate by about ≤1 to about 8 $\log_{10}$ compared to control.

8. The method of claim 1, wherein the inactivation comprises reducing the number of colony forming units (cfu) on the substrate at a rate of from about 0.05 $\log_{10}$/min to about 1.01 $\log_{10}$/min, compared to control.

9. The method of claim 1, wherein the ROS concentration in the rEWNS is from about 20 µM to about 60 µM after at a total sampling time of from about 5 minutes to about 15 minutes.

10. The method of claim 1, wherein the applying delivers a total dose of the at least one active ingredient of from about 1 pg to about 1 µg in about one hour or less.

11. A system, comprising:
    a fluid source configured to contain an aqueous composition comprising at least one active ingredient;
    an electrode;
    a conduit, coupled to the fluid source and forming an aperture, wherein at least one of the conduit and the electrode are adjustably positionable with respect to one another to set a predetermined adjustable distance from the aperture to the electrode; and
    a variable voltage source, electrically coupled between the conduit and the electrode, configured to impart an electric potential difference between the conduit and the electrode;
    wherein fluid from the fluid source that passes through conduit and the aperture is changed to enhanced engineered water nanostructures (iEWNS) upon coming into proximity of the electrode based on the predetermined distance and the electric potential, wherein the iEWNS comprise the at least one active ingredient encapsulated therein, and wherein the at least one active ingredient is present separate and in addition to any at least one active ingredient that is generated when the iEWNS are generated.

12. The system of claim 11, wherein the at least one active ingredient is at least one of reactive oxygen species (ROS) and at least one active ingredient in addition to the ROS.

13. The system of claim 11, wherein the active ingredient is an antimicrobial active ingredient.

14. The system of claim 13, wherein the antimicrobial active ingredient is at least one of hydrogen peroxide, one or more inorganic antimicrobials, one or more organic acids and salts thereof, one or more chemical antimicrobials, one or more ovo antimicrobials, one or more lacto antimicrobials, one or more bacto antimicrobials, one or more phyto antimicrobials, inorganic colloids, emulsions and combinations thereof.

15. A method, comprising:
    coupling a conduit to a fluid source configured to contain at least one active ingredient, the conduit forming an aperture,
    adjustably positioning the conduit with respect to an electrode to set a predetermined adjustable distance from the aperture to the electrode; and
    electrically coupling a variable voltage source between the conduit and the electrode, the variable voltage source configured to impart an electric potential difference between the conduit and the electrode;
    wherein fluid from the fluid source that passes through conduit and the aperture is changed to enhanced electrolyzed water engineered water nanostructures (iEWNS) comprising at least one active ingredient encapsulated therein upon coming into proximity of the electrode based on the predetermined distance and the electric potential and the at least one active ingredient is present separate and in addition to any at least one active ingredient that is generated when the iEWNS are generated.

16. The method of claim 15, wherein the active ingredient is an antimicrobial active ingredient.

17. The method of claim 16, wherein the antimicrobial active ingredient is at least one of hydrogen peroxide, one or more organic acids and salts thereof, one or more chemical antimicrobials, one or more ovo antimicrobials, one or more lacto antimicrobials, one or more bacto antimicrobials, one or more phyto antimicrobials, inorganic colloids, emulsions and combinations thereof.

18. A method for increasing shelf life of produce by increasing the firmness of the produce without altering sensory characteristics and pH, comprising treating the produce with enhanced electrolyzed water engineered water nanostructures (iEWNS) comprising at least one active ingredient encapsulated therein, wherein the at least one active ingredient is present separate and in addition to any at least one active ingredient that is generated when the iEWNS are generated.

19. A method for at least one of reducing the formation of biofilms produced by bacteria and reducing the strength of the biofilms produced by bacteria comprising:

treating a substrate comprising bacteria with enhanced electrolyzed water engineered water nanostructures (iEWNS) comprising at least one active ingredient encapsulated therein, wherein the at least one active ingredient is present separate and in addition to any at least one active ingredient that is generated when the iEWNS are generated.

20. The method of claim 19, wherein the formation of biofilm produced is reduced by at least 50%.

* * * * *

UNITED STATES PATENT AND TRADEMARK OFFICE
CERTIFICATE OF CORRECTION

| | | |
|---|---|---|
| PATENT NO. | : 11,554,190 B2 | Page 1 of 1 |
| APPLICATION NO. | : 16/640040 | |
| DATED | : January 17, 2023 | |
| INVENTOR(S) | : Demokritou et al. | |

It is certified that error appears in the above-identified patent and that said Letters Patent is hereby corrected as shown below:

In the Specification

Insert the following paragraph at Column 1, Line number 14:
--GOVERNMENT SUPPORT
This invention was made with government support under AI119481 awarded by the National Institutes of Health and 2013-67021-21075 awarded by the National Institute of Food and Agriculture. The government has certain rights in the invention.--

Signed and Sealed this
Fourth Day of February, 2025

Coke Morgan Stewart
*Acting Director of the United States Patent and Trademark Office*